(12) United States Patent
Kearns et al.

(10) Patent No.: US 11,707,430 B2
(45) Date of Patent: Jul. 25, 2023

(54) OPHTHALMIC COMPOSITIONS

(71) Applicant: The University of Liverpool, Liverpool-Merseyside (GB)

(72) Inventors: Victoria Kearns, Liverpool-Merseyside (GB); Helen Cauldbeck, Liverpool-Merseyside (GB); Steve Rannard, Liverpool-Merseyside (GB); Rachel Williams, Liverpool-Merseyside (GB); Maude Le Hellaye, Saint Justin (FR)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 327 days.

(21) Appl. No.: 16/324,271

(22) PCT Filed: Aug. 9, 2017

(86) PCT No.: PCT/GB2017/052355
§ 371 (c)(1),
(2) Date: Feb. 8, 2019

(87) PCT Pub. No.: WO2018/029476
PCT Pub. Date: Feb. 15, 2018

(65) Prior Publication Data
US 2019/0175497 A1 Jun. 13, 2019

(30) Foreign Application Priority Data
Aug. 9, 2016 (GB) ...................................... 1613695

(51) Int. Cl.
*A61K 9/00* (2006.01)
*A61K 31/203* (2006.01)
(Continued)

(52) U.S. Cl.
CPC .......... *A61K 9/0048* (2013.01); *A61K 31/192* (2013.01); *A61K 31/203* (2013.01);
(Continued)

(58) Field of Classification Search
CPC .. A61K 9/0048; A61K 31/203; A61K 31/192; A61K 47/10; A61K 47/44;
(Continued)

(56) References Cited

U.S. PATENT DOCUMENTS 5,672,355 A   9/1997  Refojo et al.
6,344,204 B1* 2/2002  Lorant ..................... A61K 8/06
                                                    424/400

(Continued)

FOREIGN PATENT DOCUMENTS

CN   104892873 A   9/2015
WO   2002005815 A1 1/2002
(Continued)

OTHER PUBLICATIONS

Gelest, Reactive Silicones: Forging New Polymer Links, 2013 Gelest borchure, 2013, printed from http://www.gelest.com/wp-content/uploads/Goods-PDF-brochures-reactivesilicones.pdf on Mar. 14, 2021, 68 pages.*

(Continued)

*Primary Examiner* — Jianfeng Song
(74) *Attorney, Agent, or Firm* — Fox Rothschild LLP

(57) ABSTRACT

A composition comprises: a base oil; an additive comprising a copolymer comprising hydrophobic and hydrophilic units; and a drug. The copolymer may for example have a comb structure in which the hydrophobic units and hydrophilic units are pendant chains on a backbone of the copolymer. The hydrophobic units and hydrophilic units may for example comprise polydimethylsiloxane moieties and ethylene glycol residues respectively. The composition may for
(Continued)

Figure 1:
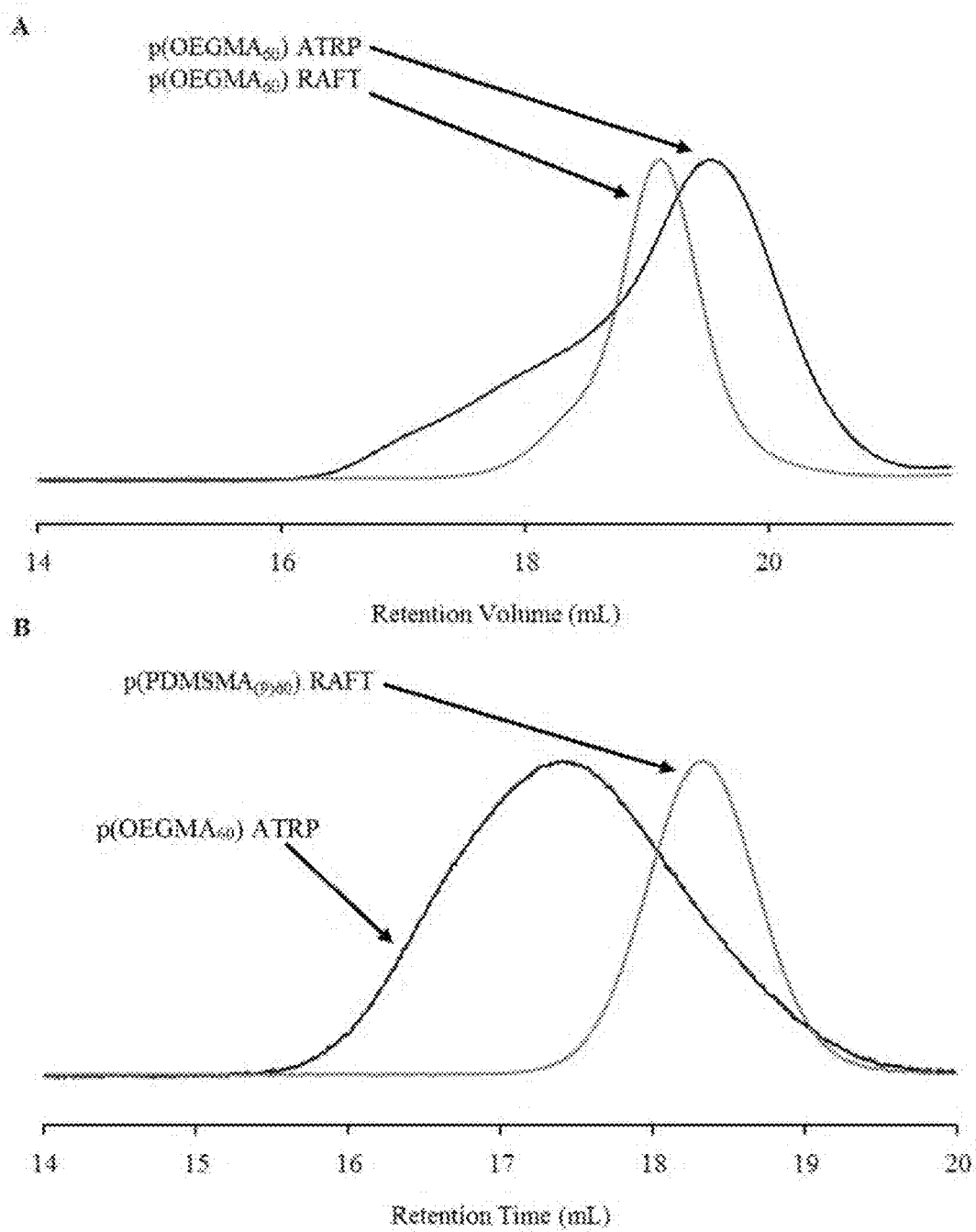

example be used as a tamponade or as a component for a tamponade administered to the eye. The invention is useful for solubilising and/or releasing drugs.

21 Claims, 9 Drawing Sheets

(51) Int. Cl.
| | | |
|---|---|---|
| A61K 31/192 | (2006.01) | |
| A61K 47/10 | (2017.01) | |
| A61K 47/32 | (2006.01) | |
| A61K 47/44 | (2017.01) | |
| A61K 47/34 | (2017.01) | |
| C08F 293/00 | (2006.01) | |
| C08F 2/38 | (2006.01) | |
| A61K 45/06 | (2006.01) | |

(52) U.S. Cl.
CPC .............. *A61K 47/10* (2013.01); *A61K 47/32* (2013.01); *A61K 47/34* (2013.01); *A61K 47/44* (2013.01); *C08F 2/38* (2013.01); *C08F 293/005* (2013.01); *A61K 45/06* (2013.01); *C08F 2438/03* (2013.01)

(58) Field of Classification Search
CPC ..... A61K 47/34; A61K 47/32; C08F 2438/03; C08F 293/005
See application file for complete search history.

(56) References Cited

U.S. PATENT DOCUMENTS

| 6,703,378 | B1 | 3/2004 | Kunzler et al. | |
|---|---|---|---|---|
| 2008/0031907 | A1* | 2/2008 | Tamarkin | A61P 17/00 514/183 |
| 2009/0053301 | A1 | 2/2009 | Lin et al. | |
| 2010/0140114 | A1* | 6/2010 | Pruitt | G02B 1/043 206/5.1 |
| 2011/0159105 | A1* | 6/2011 | Vilinsky | A61K 8/9767 424/600 |
| 2011/0208301 | A1* | 8/2011 | Anvar | C07F 7/20 623/6.13 |
| 2012/0244093 | A1* | 9/2012 | Daniels | A61K 8/342 424/59 |
| 2013/0149260 | A1 | 6/2013 | Delvalle et al. | |
| 2015/0044265 | A1* | 2/2015 | Son | A61K 36/18 424/401 |
| 2015/0182673 | A1* | 7/2015 | Delaney, Jr. | A61L 29/14 525/123 |
| 2016/0243259 | A1* | 8/2016 | Almarsson | A61K 38/00 |

FOREIGN PATENT DOCUMENTS

| WO | 2002100525 A2 | 12/2002 |
|---|---|---|
| WO | 2006122973 A1 | 11/2006 |
| WO | 2015082172 A1 | 6/2015 |

OTHER PUBLICATIONS

Sorice et al., Ascorbic acid: its role in immune system and chronic inflammation diseases, Mini Rev Med Chem, May 2014;14(5): 444-52, Abstract only, printed from https://pubmed.ncbi.nlm.nih.gov/24766384/, 1 page.*

Michels et al., Vitamin E and Skin Health, 2012. printed from https://lpi.oregonstate.edu/mic/health-disease/skin-health/vitamin-E, 19 pages.*

CAS registry, CAS Registry No. 111286-86-3 (hydroxyethyl acrylate/ sodium acryloyldimethyl taurate copolymer) with molecular formula, printed Mar. 14, 2021, 3 pages.*

Mohamed El-Rafie et al., Antioxidant and anti-inflammatory activities of silver nanoparticles biosynthesized from aqueous leaves extracts of four *Terminalia* species, Aug. 2014, Advances in Natural Sciences: Nanoscience and Nanotechnology 5(3):035008, Abstract only, 1 page.*

Wong et al., Further evidence of the anti-inflammatory effects of silver nanoparticles, ChemMedChem Jul. 2009;4(7):1129-35, printed from https://pubmed.ncbi.nlm.nih.gov/19405063/, 2 pages.*

* cited by examiner

OPHTHALMIC COMPOSITIONS

The present invention is directed towards ophthalmic compositions and components thereof. The compositions may be administered into the eye, for example within the vitreous space of the eye, for therapeutic purposes. They may be used as, or as part of, tamponades which have a physical effect. The compositions may be used to treat retinal detachment, and in procedures for treating retinal detachment such as vitrectomies.

The retina is a light-sensitive layer, which is from 0.1-0.32 mm thick and has an approximate diameter from 30-40 mm and lines the back of the interior of the eye. The main function of the retina is to direct an inverted image via a light signal, which is then converted into a communicable chemical signal by photo-transduction. The ordered pattern is then sent to the brain through the optic nerve. The centre of the retina is the only part capable of fine detailed vision.

The structure of the retina can be divided into two layers: the inner neuroretina and the outer epithelial monolayer consisting of retinal pigment epithelium, which is a layer of hexagonally close packed cells situated at the back of the human eye. The neuroretina contains photoreceptors and the retinal pigment epithelium forms an outer layer on the Bruch's membrane. The retinal pigment epithelium has several functions namely, light absorption, epithelial transport, spatial ion buffering, visual cycle, phagocytosis, secretion and immune modulation. In particular, the retinal pigment epithelium provides nutrients to the inner visual cells, as well as transporting metabolic waste to the choroid.

Retinal detachment occurs when the inner neuroretina becomes detached from the supporting retinal pigment epithelium. There are several causative factors that can result in retinal detachment, such as a traumatic event, diabetic proliferative retinopathy and cataract surgery. If the retina remains detached, it will degenerate and lose its ability to function. Thus, failure to treat retinal detachment quickly and effectively can lead to permanent localised loss of vision (e.g. central vision will be lost if the macular remains detached) or permanent loss of vision.

There are different types of retinal detachment: i) rhegmatogenous retinal detachment, which is caused by a tear or break in the retina and the accumulation of vitreous humour between the detached retina and the retinal pigment epithelium that can cause further separation between the two layers; ii) exudative retinal detachment, which is caused by a build-up of fluid from blood vessels behind the retina that may be triggered by conditions such as severe macular degeneration, very high blood pressure, and certain cancers, such as choroidal melanoma; and iii) tractional retinal detachment, which is caused by pulling on the retina that can occur as a result of, or a complication of, other conditions, such as diabetic proliferative retinopathy and proliferative vitreoretinopathy.

Proliferative vitreoretinopathy is a condition that can follow a break in the retina where a scar-like membrane formation occurs, analogous to dynamic wound healing. The scar-like tissue then creates traction that pulls the neuroretina from the supporting retinal pigment epithelium, which leads to tractional retinal detachment.

Traumatic proliferative vitreoretinopathy occurs at the vitreoretinal interface and it results from a perforating trauma to the posterior segment of the eye, or it can happen following surgical intervention. Proliferative vitreoretinopathy is a complication that follows rhegmatogenous retinal detachment, especially if there has been a severe retinal tear. Proliferative vitreoretinopathy occurs in approximately 5-10% of all rhegmatogenous retinal detachments, and proliferative vitreoretinopathy is also implicated in re-detachment after surgery in 75% of cases, making proliferative vitreoretinopathy the most common cause of failure of rhegmatogenous retinal detachment surgery.

During trauma or rhegmatogenous retinal detachment, the retinal pigment epithelium loses contact with adjacent cells, and consequently loses cellular signalling. The retinal pigment epithelium then comes into contact with different growth factors and cytokines, triggering the cells to proliferate, de-differentiate and migrate to repair the defect. The retinal pigment epithelium cells undergo epithelial-mesenchymal transition where the microvilli retract causing a loss of adhesion to the neuroretina and their extracellular matrix. The cells then round up and detach from their basement membrane. Retinal pigment epithelium cells then de-differentiate into wound repair phenotypes, similar to fibroblasts and macrophages which construct a membrane, as they migrate towards the vitreous space. This differentiation is regulated by various growth factors (platelet-derived growth factor, TGF-ß, epidermal growth factor, tumour necrosis factor alpha, FGF and others) as well as cytokines (interleukin 1, 6, 8, 10 and interferon-gamma). Retinal pigment epithelium cells are the main component of the membranes. However, other cells involved include fibroblasts, which are responsible for tissue repair, in particular scar formation, myofibroblasts and macrophages, as well as minor amounts of glial cells. The resulting membranes contract and distort/pull on the retina leading to tractional retinal detachment.

There are numerous ways in which retinal detachment can be treated, which all have the underlying aim of reattaching the retina to the retinal pigment epithelium and fixing any tears or breaks that may be present in the retina. One such treatment is vitrectomy followed by the insertion of a tamponade, which fills the vitreous space.

A vitrectomy is the surgical removal of the vitreous liquid from the eye, which involves the removal of the vitreous liquid through small cuts in the sclera. The vitreous liquid is then replaced by saline, which itself can be subsequently replaced by air, gas or a silicone oil tamponade. The tamponade prevents access of any remaining aqueous components to the site of the tear, which inhibits migration of any aqueous components into the sub-retinal space, excluding any inflammatory factors and initiating retinal detachment.

Air and gas are temporary tamponades that last anywhere from days (e.g. in the case of air) to weeks, depending on the gas used (e.g. perfluorocarbon gases have a residency of two-three weeks). However, during the use of air or gas tamponades, the patient should lie predominantly facing downwards for a period of 4 weeks to ensure that the air or gas bubble is aligned with the damaged region and any remaining vitreous material is held away from the repair site as the motion of the viscous fluid may lead to greater damage. Silicone oils and derivatives thereof, on the other hand, are the only class of long term tamponades whose effects do not dissipate over time. It is, however, necessary to remove the silicone oil after the initial surgery (e.g. two to eight months after the initial surgery).

Alternatives to silicone oils have been investigated. One such alternative is fluorinated silicone oil. The specific gravity of fluorinated silicone oil can be tailored depending on the ratio of fluorinated silicone oil to silicone oil, but the low viscosity of fluorinated silicone oil can cause a macrophagic response. It is also not automatically safe to use highly viscous fluorinated silicone oil as white deposits on the retina have been observed with materials of 1750 mPa·s.

Other additives to silicone oil have been investigated, such as semi-fluorinated alkanes, which are transparent and immiscible with water. Semi-fluorinated alkanes act as an amphiphilic surfactant as the hydrocarbon end is highly hydrophobic whereas the fluorocarbon end is less hydrophobic. The specific gravity of semi-fluorinated alkanes can be determined by the length of the alkane chain. The use of semi-fluorinated alkanes in a clinical environment as the sole tamponade agent has been restricted because of dispersion effects, which can induce a macrophagic response. Accordingly, studies using mixtures of semi-fluorinated alkanes with silicone oils have been undertaken. In those studies, the solubility of the semi-fluorinated alkanes was found to be determined by the viscosity of the silicone oil and the molecular weight of the semi-fluorinated alkanes, and increasing either will reduce the solubility of the semi-fluorinated alkanes.

It has been found that additional treatments are required in certain circumstances. For example, when treating proliferative vitreoretinopathy, corticosteroids may be administered intravitreally to combat the inflammatory response caused by a break or tear in the retina. However, corticosteroids can also be applied topically, subconjunctival injections and, less frequently, sub-tenon injections, orbital floor injections or retrobulbar injections. The tensional forces can be relieved by surgery, which removes scar tissue that has formed and is referred to as membrane pealing. A vitrectomy is usually performed at the same time as the membrane peeling.

In the event that retinal reattachment is not achieved quickly and effectively, there remains no effective preventative treatment for proliferative vitreoretinopathy. This may be attributable to the difficulty in achieving therapeutic drug levels in the vitreous space and retina through conventional routes of administration. It is possible to administer drugs intravitreally or subconjunctivally, but proliferative vitreoretinopathy is a long term condition that requires treatment over a period of several weeks and the half-life of most drugs in the vitreous space or subconjunctival cavity is short. Further, repeated injections can cause complications, such as infections, inflammation and elevated intraocular pressure and/or a build-up of drug to toxic levels.

To date, various pharmacological agents have been investigated to reduce and/or prevent proliferative vitreoretinopathy. The two main categories are anti-inflammatory and anti-proliferative drugs, but studies have also been performed with antioxidants, antineoplastic and antigrowth factors, alone and as combination therapies of two or more drugs. There has not, however, been a satisfactory way in which to administer drugs. The existing drug delivery devices suffer from a multitude of drawbacks, such as the poor solubility of drugs in silicone oil, the inherent low solubility of silicone-soluble drugs in water, a restricted range of silicone soluble excipient materials to moderate release, difficulties in directly assessing drug concentrations within the oil phase, limitations in drug content and release amounts (in the case of contact lenses), release of the drugs too quickly or too soon (in the case of liposomes and inserts), difficulty to reverse in the event of adverse effects (in the case of micro- and nano-particles), and the potential to cause infections (in the case of explants, such as scleral buckles).

There therefore remains a need for a new and improved composition that can be used to treat eye disorders, which does not suffer from the drawbacks of the prior art and existing approaches. Specifically, there remains a need for a composition that can be used to prevent or treat disorders, such as proliferative vitreoretinopathy, and effectively deliver drugs over a prolonged period in non-toxic amounts. However, the eye is a complex organ with unique barriers that limit fluid transport, and hence drug delivery from conventional topical or systemic routes is challenging. The eye is also isolated by blood-retinal and blood-aqueous barriers, which presents unique challenges. It has been found, nonetheless, that the composition of the present invention, which comprises a base oil, an additive comprising a copolymer comprising hydrophobic and hydrophilic monomeric units and a drug, achieves the desired effects of safely and effectively delivering drugs over a prolonged period. Advantageously, the amounts delivered over a prolonged period of time are also non-toxic.

Thus, according to a first aspect of the present invention, there is provided a composition comprising:
 a base oil;
 an additive comprising a copolymer comprising hydrophobic and hydrophilic units; and
 a drug.

The present invention is particularly advantageous because the components that are used are intended to be non-toxic. The compositions are also advantageous because they have an advantageous effect in solubilising and releasing drugs in addition to a physical filling effect.

Thus the composition may be an ophthalmic composition, e.g. a composition suitable for application into the eye or suitable for application to a tamponade, or an ophthalmic tamponade itself.

In one arrangement, any suitable base oil may be used, such as a silicone oil, a fluorinated silicone oil or a perfluorocarbon oil. The base oil may comprise one or more silicone oils, fluorinated silicone oils, perfluorocarbon oils, or mixtures thereof. Alternatively, the base oil may comprise exclusively silicone oil, fluorinated silicone oil or perfluorocarbon oil. The silicone oil may be polydimethylsiloxane. In one arrangement, the base oil may comprise purified polydimethylsiloxane, such as $SiO_{1000}$, $SiO_{5000}$ or the commercial products Siluron® 2000, Siluron® 5000 and Siluron® 1000, which are obtained from Fluron® GmBH of Magirus-Deutz-Straß 10, 89077 Ulm, Germany, or the commercial products Sil-1000® and Sil-5000®, which are obtained from D.O.R.C. Dutch Ophthalmic Research Center (International) B.V. of P.O. Box 43, 3214 ZG Zuidland, The Netherlands, or the commercial products Oxane 1300 and Oxane 5700, which are obtained from Bausch+Lomb, 106 London Road, Kingston upon Thames, Surrey, KT2 6TN, England, or mixtures thereof. In another arrangement, the base oil may comprise a high-density silicone oil that comprises polydimethylsiloxane and perfluorohexyloctane, such as the commercial products Densiron® 68, Densiron® Xtra and Siluron® Xtra. It will be understood that other equivalent commercial products could be used that achieve a similar technical effect.

The kinematic viscosity of different types of base oils, such as polydimethylsiloxane base oils or a high-density silicone oils that comprise polydimethylsiloxane and perfluorohexyloctane, is expressed in centistokes (1 cSt=$10^{-6}$ m$^2$/s), and arises from both the molecular weight and the length of the polymer; increasing SiO molecular weight results in an increased polymer chain length and consequently an increased viscosity. In one arrangement, the kinematic viscosity of the base oil may range from about 100 to about 10,000 cSt, form about 200 to about 9,500 cSt, from about 300 to about 9,000 cSt, from about 400 to about 8,500 cSt, from about 500 to about 8,000 cSt, from about 600 to about 8,500 cSt, from about 700 to about 7,000 cSt, from about 800 to about 6,500 cSt, from about 900 to about 6,000 cSt, from about 950 to about 5,500 cSt, from about 1,000 to about 5,000 cSt, from about 1,100 to about 4,900 cSt, from about 1,200 to about 4,800 cSt, from about 1,300 to about 4,700 cSt, from about 1,400 to about 4,600 cSt, from about 1,500 to about 4,500 cSt, from about 1,700 to about 4,300 cSt, from about 1,900 to about 4,100 cSt, from about 2,000 to about 4,000 cSt, from about 2,200 to about 3,800 cSt, from about 2,400 to about 3,600 cSt, from about 2,600 to about 3,400 cSt, or from about 2,800 to about 3,200 cSt. In another arrangement, the kinematic viscosity of the base oil may be about 500 cSt, about 600 cSt, about 700 cSt, about 800 cSt, about 900 cSt, about 1,000 cSt, about 1,100 cSt, about 1,200 cSt, about 1,300 cSt, about 1,400 cSt, about 1,500 cSt, about 1,700 cSt, about 1,900 cSt, about 2,100 cSt, about 2,300 cSt, about 2,500 cSt, about 2,700 cSt, about 2,900 cSt, about 3,100 cSt, about 3,300 cSt, about 3,500 cSt, about 3,700 cSt, about 3,900 cSt, about 4,100 cSt, about 4,300 cSt, about 4,500 cSt, about 5,000 cSt, about 6,000 cSt, about 7,000 cSt, about 8,000 cSt, about 9,000 cSt, about 10,000 cSt.

The use of an additive comprising a copolymer comprising hydrophilic and hydrophobic units is particularly advantageous because the units can interact with the drug in the base oil and with the additive by hydrogen-bonding, for example. These interactions can yield advantageous properties, such as improving the solubility of the drug in the base oil and/or modifying the release rate of the drug from the base oil, such that the drug is released over a prolonged period of time. Without wishing to be bound by theory, it is thought that these advantageous properties are brought about by localised interactions between the hydrophilic units of the additive and the drug, and between the hydrophobic units of the additive and the base oil. In an alternative theory, it is thought that the additive could bring about a bulk effect in the composition that alters the solubility of the drug in the base oil.

In the absence of an additive, the free drug would need to be released solely by diffusion through the oil, which has been found to happen in an uncontrolled manner over the period of a week in vivo in a rabbit model based study. This is not advantageous in view of the treatment times that are typically involved for treating ocular conditions.

In one arrangement, the copolymer may be amphiphilic. The use of an amphiphilic copolymer instead of a pure hydrophilic polymer, such as polyethylene glycol, is particularly advantageous because a polymer formed from only hydrophilic monomers would be practically insoluble in the base oil.

The copolymer may comprise any suitable hydrophilic unit. Any suitable hydrophilic unit may be used, such that it is capable of being paired with the drug, for example the hydrophilic unit forms hydrogen bonds with the drug. In one arrangement, the hydrophilic unit may be a polyethylene glycol unit, a poly(N-(2-hydroxypropyl)methacrylamide) unit, a polyvinylpyrrolidone unit, a polylysine unit. The hydrophilic unit may impart amphiphilic character to the copolymer and allow localisation at the interface of the base oil and aqueous layer.

In one arrangement, the copolymer is formed from monomers comprising a hydrophilic monomer unit. Any suitable hydrophilic monomer unit may be used, such that it is capable of being paired with the drug, for example the hydrophilic monomer unit forms hydrogen bonds with the drug. The hydrophilic monomer unit may be any suitable monomer. In a further arrangement, the hydrophilic monomer unit may comprise an oligoethyleneglycol methacrylate monomer, such as an oligoethyleneglycol monomethyl ether methacrylate monomer, a N-(2-hydroxy propyl) methacrylamide monomer, a N-vinylpyrrolidone monomer, or a lysine monomer.

The copolymer may comprise any suitable hydrophobic unit. In one arrangement, the hydrophobic unit may be miscible with the base oil, and it may, for example, be selected from a methacrylate monomer, dimethacrylate monomer, or mixtures thereof. The hydrophobic unit may improve solubility of the drug in the base oil.

In one arrangement, the copolymer is formed from monomers comprising a hydrophobic monomer unit. The hydrophobic monomer unit may be any suitable monomer. In a further arrangement, the hydrophobic monomer unit may be miscible with the base oil, and it may, for example, comprise a polydimethylsiloxane acrylate monomer, such as polydimethylsiloxane methacrylate monomer or polydimethylsiloxane dimethacrylate monomer, or mixtures thereof.

Any suitable number of different monomeric units may be used to form the copolymer. In one arrangement, the copolymer may be amphiphilic such that it comprises at least one hydrophilic monomeric unit and at least one hydrophobic monomeric unit. In one arrangement, the copolymer may comprise: from about 4 to about 100 hydrophobic monomeric units; from about 5 to about 90 hydrophobic monomeric units; from about 10 to about 80 hydrophobic monomeric units; from about 15 to about 70 hydrophobic monomeric units; from about 20 to about 60 hydrophobic monomeric units; or from about 25 to about 50 hydrophobic monomeric units. In another arrangement, the copolymer may comprise: from about 4 to about 100 hydrophilic monomeric units; from about 5 to about 90 hydrophilic monomeric units; from about 10 to about 80 hydrophilic monomeric units; from about 15 to about 70 hydrophilic monomeric units; from about 20 to about 60 hydrophilic monomeric units; or from about 25 to about 50 hydrophilic monomeric units. In yet another arrangement, the copolymer may independently comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 hydrophilic monomeric units and hydrophobic monomeric units.

It will be understood that any combination of hydrophilic and hydrophobic monomeric units may be present, and are envisaged by the disclosure herein. For example, the copolymer may comprise from about 4 to about 100 hydrophobic monomeric units and from about 10 to about 80 hydrophilic monomeric units or the copolymer may comprise from about 20 to about 60 hydrophobic monomeric units and about 25 to about 50 hydrophilic monomeric units. Similarly, the copolymer may comprise from 26 hydrophilic monomeric units and 35 hydrophobic monomeric units or 42 hydrophilic monomeric units and 31 hydrophobic monomeric units. Other combinations are envisaged and would be readily understood by the skilled person.

Any suitable molar ratios of hydrophilic to hydrophobic monomeric units may be used in the formation of the copolymer. In one arrangement, the molar ratios of the two monomeric units (hydrophobic:hydrophilic) may be from 80:20 to about 50:50; from about 75:25 to about 50:50; from about 70:30 to about 50:50; from about 65:35 to about 50:50; from about 60:40 to about 50:50; or from about 55:45 to about 50:50.

The copolymer may have any suitable molecular weight. In one arrangement, the copolymer may have a weight average molecular weight ($M_w$) of from about 30,000 to about 5,300,000 g/mol. In another arrangement, the copolymer may have a weight average molecular weight of from about 35,000 to about 5,000,000 g/mol, from about 40,000 to about 3,600,000 g/mol, from about 45,000 to about 500,000 g/mol, from about 50,000 to about 450,000 g/mol, from about 55,000 to about 400,000 g/mol, from about 60,000 to about 350,000 g/mol, from about 65,000 to about 300,000 g/mol, from about or 70,000 to about 250,000 g/mol, or from about or 75,000 to about 200,000 g/mol.

The additive may be, or may comprise, a vinyl polymer, i.e. may be formed by the polymerisation of double bond—containing monomers to form carbon-carbon polymer backbones.

Thus the hydrophobic unit(s) of the copolymer may be derived from monomers which have not only a double bond but also a hydrophobic part e.g. a polydimethylsiloxane part. For example, hydrophobic units may comprise pendant PDMS chains on a carbon-carbon chain (i.e. vinyl polymer chain). Parts of the additive can therefore be formed from monomers which have a double bond (e.g. a methacrylate moiety, or other vinyl moiety) linked to e.g. a PDMS chain or other hydrophobic moiety.

Similarly the hydrophilic unit(s) of the copolymer may be derived from monomers which have not only a double bond but also a hydrophilic part e.g. an ethylene glycol (e.g. polyethylene glycol or oligoethylene glycol) unit. For example, hydrophilic units may comprise pendant OEG or PEG chains on a carbon-carbon chain (i.e. vinyl polymer chain). Parts of the additive can therefore be formed from monomers which have a double bond (e.g. a methacrylate moiety, or other vinyl moiety) linked to e.g. an OEG chain or PEG chain or other hydrophilic moiety.

Thus the architecture of the copolymer, or part of it, may be a comb structure.

The copolymer may be a block copolymer or statistical copolymer or make take other forms.

The copolymer may be linear or branched. In one arrangement, where the copolymer is branched, any suitable agent to facilitate branching may be used, such as a multifunctional vinyl brancher, for example a divinyl monomer, or a dimethacrylate brancher, such as polydimethylsiloxane dimethacrylate. The branching agent may be present in any suitable amount. In a further arrangement, the molar ratio of the initiator to the branching agent (initiator:branching agent) used to form the polymer is less than 1:1 to avoid gelation. In one arrangement, the molar ratio of initiator to the branching agent (initiator:branching agent) used to form the polymer may be from about 1:0.95 to about 1:0.05, from about 1:0.90 to about 1:0.10, from about 1:0.0.85 to about 1:0.15, from about 1:0.80 to about 1:0.20, from about 1:0.75 to about 1:0.25, from about 1:0.70 to about 1:0.30, from about 1:0.65 to about 1:0.40, from about 1:0.60 to about 1:0.45, or from about 1:0.55 to about 1:0.50.

The multifunctional monomer may also comprise a hydrophobic part (e.g. a PDMS chain) or a hydrophilic part (e.g. an ethyleneglycol part), so that it may not only function as a brancher but may also contribute hydrophobic or hydrophilic properties to the additive.

The additive may be present in the composition in any suitable amount. In one arrangement, the additive may be present in an amount of from about 0.05% to about 20% v/v relative to the base oil. In another arrangement, the additive may be present in an amount of from about 1% to about 15% v/v, from about 2% to about 12% v/v, from about 3% to about 10% v/v, from about 4% to about 8% v/v, from about 4% to about 7% v/v, where the % v/v is relative to the base oil. In another arrangement, the additive may be present in an amount of 0.05% v/v, 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, where the % v/v is relative to the base oil.

In one arrangement, the copolymer may comprise residues of polydimethylsiloxane dimethacrylate units, containing repeating SiO units, as follows:

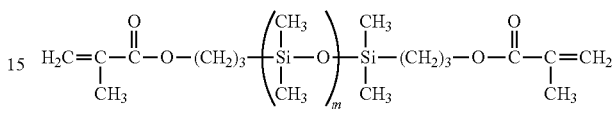

M may be any suitable number. In one arrangement, m may be selected from about 1 to about 300. In another arrangement, m may be selected from about 5 to about 290, from about 10 to about 280, from about 20 to about 250, from about 20 to about 200, from about 30 to about 180, from about 40 to about 150 or from about 50 to about 100. In a further arrangement, m may be selected from 1, 2, 4, 6, 8, 10, 12, 14, 16, 18, 20, 25, 30, 35, 40, 45, 50, 55, 60, 65, 70, 80, 90, 100, 150, 200, 250, 282, or 300.

In another arrangement, the copolymer may comprise residues of polydimethylsiloxane methacrylate, containing repeating SiO units, as follows:

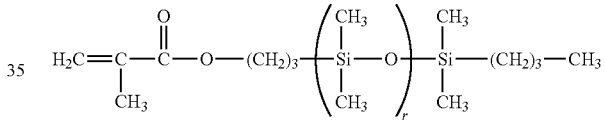

R may be any suitable number. In one arrangement, r may be selected from about 1 to about 100. In another arrangement, r may be selected from about 2 to about 90, from about 4 to about 85 from about 6 to about 80, from about 8 to about 75, from about 8 to about 70, from about 9 to about 65, from about 10 to about 60, from about 12 to about 57, or from about 14 to about 55. In a further arrangement, r may be selected from 1, 2, 3, 4, 5, 6, 7, 8, 9, 10, 11, 12, 14, 16, 18, 20, 25, 30, 35, 40, 45, 50, 55, 57, 60, 65, 70, 75, 80, 85, 90, 95, or 100. It will be appreciated that the molecular weight of the copolymer will, of course, change with the value of r. For example, an r value of 9 correlates to a molecular weight of 985 gmol$^{-1}$ and an r value of 57 correlates to a molecular weight of 4,600 gmol$^{-1}$.

The skilled person will understand that, in order to obtain a linear vinyl polymer unit containing hydrophobic monomer residues, the polydimethylsiloxane methacrylate drawn above, for example, may be vinyl polymerised.

The skilled person will further understand that, in order to obtain a branched vinyl polymer unit containing hydrophobic monomer residues, the polydimethylsiloxane methacrylate drawn above, for example, may be vinyl polymerised, together with the polydimethylsiloxane dimethacrylate drawn above, for example.

The copolymer may be prepared by any suitable polymerisation method. In one arrangement, the copolymer may be prepared by controlled radical polymerisation. The controlled radical polymerisation method may be selected from: atom transfer radical polymerisation; nitroxide mediated polymerisation; or reversible addition-fragmentation chain transfer. In one arrangement, the controlled radical polymerisation method may be selected from atom transfer radical polymerisation or reversible addition-fragmentation chain transfer. Atom transfer radical polymerisation and reversible addition-fragmentation chain transfer are capable of polymerising a wide range of monomer functionalities within a range of solvent environments, whereas nitroxide mediated polymerisation, which is particularly useful for some monomers, is limited to the functionality that it can tolerate.

All three controlled radical polymerisation methods mentioned above present similar mechanistic principles whereby an active species, capable of monomer addition, is in dynamic equilibrium with its dormant state, which is inert to polymerisation. Each method ensures that the concentration of the active species remains low throughout polymerisation, which helps to minimise undesirable reactions, such as chain transfer and chain termination. Only when this is achieved does the polymerisation react in a controlled manner; slow monomer addition is ensured allowing the polymer chains to grow in a more uniform manner, therefore, minimising dispersity within the molecular weight distribution.

In another embodiment, the copolymer may be prepared by reversible addition/fragmentation chain transfer, which is a form of controlled radical polymerisation that relies on the use of a chain transfer agent to control the process of monomer addition. Reversible addition/fragmentation chain transfer agents utilise sulphur chemistry to interact with propagating radicals. The use of this technique can overcome some challenges in incorporating a water-soluble polymer into copolymer that is to be introduced into a non-polar base oil environment.

The chain transfer agents may be produced by any suitable synthetic approach. In one arrangement, the structure of the chain transfer agent may be based around a thiocarbonylthio group capped at each side with groups that are commonly referred to as the R and Z groups. The groups that may be present as the R and Z groups include dithioesters, such as dithiobenzoates, trithiocarbonates and dithiocarbamates, such as xanthates, and specific compounds such as 2-cyano-2-propyl benzodithioate. Following polymerisation the α-terminus of the polymer chain may be capped with the R group, while the Z group may cap the ω-end of the polymer chain. The chemical structure of the reversible addition/fragmentation chain transfer agent dictates the monomer functionality to which it is best suited to polymerise, for example, highly activated reversible addition/fragmentation chain transfer agents, such as xanthates, are used to polymerise less activated monomers, such as vinyl acetate. Alternatively, more activated monomers, such as methacrylates, can be polymerised with good control by less activated reversible addition/fragmentation chain transfer agents, such as trithiocarbonates and dithioesters.

In an alternative arrangement, it is possible to prepare branched polymers by reversible addition/fragmentation chain transfer polymerisation using a method that utilises the polymer backbone as a scaffold from which polymer chains are grown. This process can be used to produce comb-like structures via copolymerisation with a monomer that can easily be modified into a reversible addition/fragmentation chain transfer agent. Branched polymers may, for example, be produced via the copolymerisation of vinyl and divinyl functionalised monomers in the presence of a reversible addition/fragmentation chain transfer agent.

In one arrangement, where an initiator is used, the molar ratio of chain transfer agent to initiator may be less than or equal to about 1:0.1. In another arrangement, where an initiator is used, the molar ratio of chain transfer agent to initiator may be about 1:0.1, about 1:0.08, about 1:0.06, about 1:0.04, or about 1:0.02. Alternatively, the molar ratio of chain transfer agent to initiator used may be from about 1:0.2 to about 1:0.02, from about 1:0.1 to about 1:0.04, or from about 1:0.08 to about 1:0.06. Any suitable initiator may be used. In one arrangement, the initiator may be selected from 2,2'-azobis(2-methylpropionitrile), 4,4'-azobis(4-cyanovaleric acid) and 4,4'-azobis(4-cyanopentanoic acid).

Before arriving at the present invention, the inventors investigated the preparation of prodrugs of all-trans retinoic acid and ibuprofen based on poly(ethylene oxide) and silicone oil for ophthalmic drug delivery.

In one arrangement, any suitable drug may be used. The drug may be present as the free drug, for example in neutral, acidic or basic form. The drug may be an anti-inflammatory drug, an anti-proliferative, an anti-oxidant drug, an anti-neoplastic drug, an anti-growth factor or mixtures thereof. In one arrangement, the drug may be selected from an anti-inflammatory drug, an anti-proliferative, an anti-oxidant drug, or mixtures thereof. In another arrangement, the drug may be selected from anti-proliferative drugs, such as all-trans retinoic acid, 5-flurouracil, α-tocopherol, dasatinib, daunorubicin, daunomycin, doxorubicin and mitomycin, or anti-inflammatories, such as non-steroidal anti-inflammatories, e.g. ibuprofen. In one arrangement, the drug may be all-trans retinoic acid. In an alternative arrangement, the drug may be ibuprofen.

Retinoic acid is particularly advantageous when used in the present invention because it has anti-proliferative and anti-oxidant effects and it is known to reduce proliferative vitreoretinopathy and retinal pigment epithelium cell proliferation, as well as being used to treat leukaemia and acne. Retinoic acid is a derivative of vitamin A, which is already present in the eye and plays a role in the visual cycle and so its use is particularly advantageous. Retinoic acid also is less aggressive than some other anti-proliferative drugs, such as 5-fluorouracil, and it is soluble in silicone oil. Ibuprofen is particularly advantageous because it is a non-steroidal anti-inflammatory drug that is widely used for pain relief. Ibuprofen is soluble in silicone oil.

In some arrangements, the drug may be conjugated to the additive. Any suitable conjugation method may be used. In another arrangement, the drug may be conjugated to the additive by one or more covalent bonds. Alternatively, the drug may be conjugated to the linker by a single covalent bond.

Administration and Treatment

The present invention provides a method of preventing or treating an eye disorder in a human or animal subject. The present invention also provides compositions for use in a method of preventing or treating an eye disorder in a human or animal subject. The present invention also provides compositions for use in a method of manufacturing a medicament for preventing or treating an eye disorder in a human or animal subject. The methods, uses in methods and compositions disclosed herein may comprise administering to the human or animal subject a therapeutically effective amount of the composition, as defined in the present invention.

In one arrangement, the eye disorder may be a retinal disease, condition or disorder, such as proliferative retinal pigment epithelium diseases, a detached retina, a torn retina or a disease, condition or disorder associated with an abnormality in the retinal pigment epithelium or its function. In another arrangement, the eye disorder may be proliferative vitreoretinopathy, retinal pigment epithelium cell proliferation or proliferative diabetic retinopathy. In a further arrangement, the detached or torn retina may be caused by rhegmatogenous retinal detachment, exudative retinal detachment, or tractional retinal detachment.

The composition of the present invention involves administration of a drug of the present invention to a subject. The drug may be administered in a therapeutically effective amount.

The composition of the invention may act as a tamponade. It is however not essential for the composition to act as a tamponade, or to act as a tamponade on its own: optionally a relatively small amount of composition may be used for the purpose of delivering a drug.

The term "therapeutically effective amount" or "therapeutically effective dose" as used herein refers to an amount of a drug needed to: treat; ameliorate; prevent the targeted disease condition; exhibit a detectable therapeutic or preventative effect. Toxicity and therapeutic efficacy of drugs can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The therapeutically effective amount or therapeutically effective dose is the amount of the drug that will elicit the biological or medical response of a tissue, system, animal, or human that is being sought by the researcher, veterinarian, medical doctor, or other clinician. For example, anti-proliferative activity or anti-inflammatory activity in the treatment and/or prevention of eye disorders, e.g. proliferative vitreoretinopathy.

Dosages preferably fall within a range of circulating concentrations that includes the $ED_{50}$ with little or no toxicity. Dosages may vary within this range. The exact formulation and dosage should be chosen according to methods known in the art, in view of the specifics of a patient's condition.

Dosage amount may be adjusted individually to provide levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration.

In general, the therapeutically effective dose/amount can be estimated by using conventional methods and techniques that are known in the art. Initial doses used in animal studies (e.g. non-human primates, mice, rabbits, dogs, or pigs) may be based on effective concentrations established in cell culture assays. The animal model may also be used to determine the appropriate concentration range. Such information can then be used to determine useful doses in human patients.

The specific dosage level required for any particular patient will depend on a number of factors, including severity of the condition being treated, the general health of the patient (i.e. age, weight and diet), the gender of the patient, the time of administration, judgement of the prescribing physician and tolerance/response to therapy. In general, however, the drug may be present in an amount of from about 1 to about 1000 µg per ml, from about 5 to about 900 µg per ml, from about 10 to about 800 µg per ml, from about 15 to about 700 µg per ml, from about 20 to about 600 µg per ml, from about 25 to about 500 µg per ml, or from about 30 to about 400 µg per ml.

In one arrangement, the drug may be released over a period of from about 2 to about 10 weeks, from about 3 to about 9 weeks, from about 4 to about 8 weeks, or from about 5 to about 7 weeks. In another arrangement, the drug may be released over a period of about 2, about 3, about 4, about 5, about 6, about 7, about 8, about 9 or about 10 weeks.

The present compositions may, if desired, be provided in a pack or dispenser device containing one or more unit dosage forms containing the composition. Such a pack or device may, for example, comprise metal or plastic or glass and rubber stoppers, such as in vials. Alternatively, the device may be a pre-loaded syringe and the pack may comprise one or more pre-loaded syringes. The pack or dispenser device may be accompanied by instructions for administration. The compositions of the invention may be formulated in a compatible pharmaceutical carrier or they may also be prepared, placed in an appropriate container, and labelled for treatment of an indicated condition.

It will be understood that any combination of doses and time periods is envisaged by the disclosure herein. For example, the drug may be present in an amount of from about 1 to about 1000 µg per ml and released over a period of from about 2 to about 10 weeks. Similarly, the drug may be present in an amount of from about 10 to about 800 µg per ml and released over a period of from about 4 to about 8 weeks.

Definitions

The term "copolymer" refers to a polymer made up of more than one (type of) monomer. The copolymer may include two or more monomers, e.g. it can be a terpolymer. The copolymer may be amphiphilic, such that at least one monomer is hydrophobic, for example polydimethylsiloxane, and at least one monomer is hydrophilic, for example polyethylene glycol.

Reference herein to "ibuprofen" is a reference to (RS)-2-(4-(2-Methylpropyl)phenyl)propanoic acid, which is shown below.

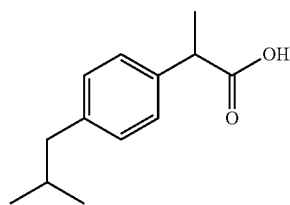

Reference herein to "all-trans retinoic acid" is a reference to (2E,4E,6E,8E)-3,7-Dimethyl-9-(2,6,6-trimethylcyclohexen-1-yl)nona-2,4,6,8-tetraenoic acid, which is shown below.

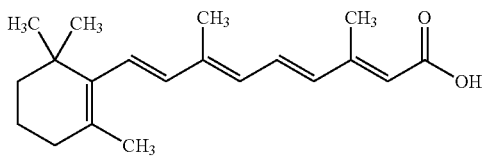 [SMILES: CC1=C(/C=C/C(C)=C/C=C/C(C)=C/C(=O)O)C(C)(C)CCC1]

The use of the word "a" or "an" when used in conjunction with the term "comprising" in the claims and/or the specification may mean "one," but it is also consistent with the meaning of "one or more," "at least one," and "one or more than one". Throughout this application, the term "about" is used to indicate that a value includes the inherent variation of error for the device, the method being employed to determine the value.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open ended and do not exclude additional, un-recited elements or method steps.

The terms "comprising" encompasses the term "consisting" e.g. a composition "comprising" X may consist exclusively of X or may include something additional e.g. X+Y, and "consisting essentially of", e.g. a composition "comprising" X may consist essentially of X or may include X and an additional amount of one or more impurities for example.

"Optional" or "optionally" means that the subsequently described event or circumstances may or may not occur, and that the description includes instances where said event or circumstance occurs and instances in which it does not.

"May" means that the subsequently described event of circumstances may or may not occur, and that the description includes instances where said event or circumstance occurs and instances in which it does not.

The term "SiO" refers to silicone oil. For example, $SiO_{1000}$ refers to a silicone oil having a kinematic viscosity of 1000 CSt, and $SiO_{5000}$ refers to a silicone oil having a kinematic viscosity of 5000 CSt. Similarly, $SiO_{1000-5000}$ refers to a Silicone oil having a kinematic viscosity of from 1000-5000 CSt.

All rheological measurements, including measurement of kinematic viscosity, were carried out using a TA Instruments Rheolyst AR 1000 N controlled-stress rheometer (TA Instruments, Elstree, United Kingdom). A 50 mm diameter, 4° steel cone geometry was used. All measurements were carried out at 37° C. Temperature control of the rheometer is achieved via a plate that utilises the Peltier effect to control the temperature of the sample within ±0.1° C. Shear viscosity was calculated from the gradient of the plot of shear stress against shear rate.

Where the compounds according to this invention have at least one chiral centre, they may accordingly exist as enantiomers. Where the compounds possess two or more chiral centres, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

It is to be understood that all such isomers and mixtures thereof are encompassed within the scope of the present invention.

Figure 2:
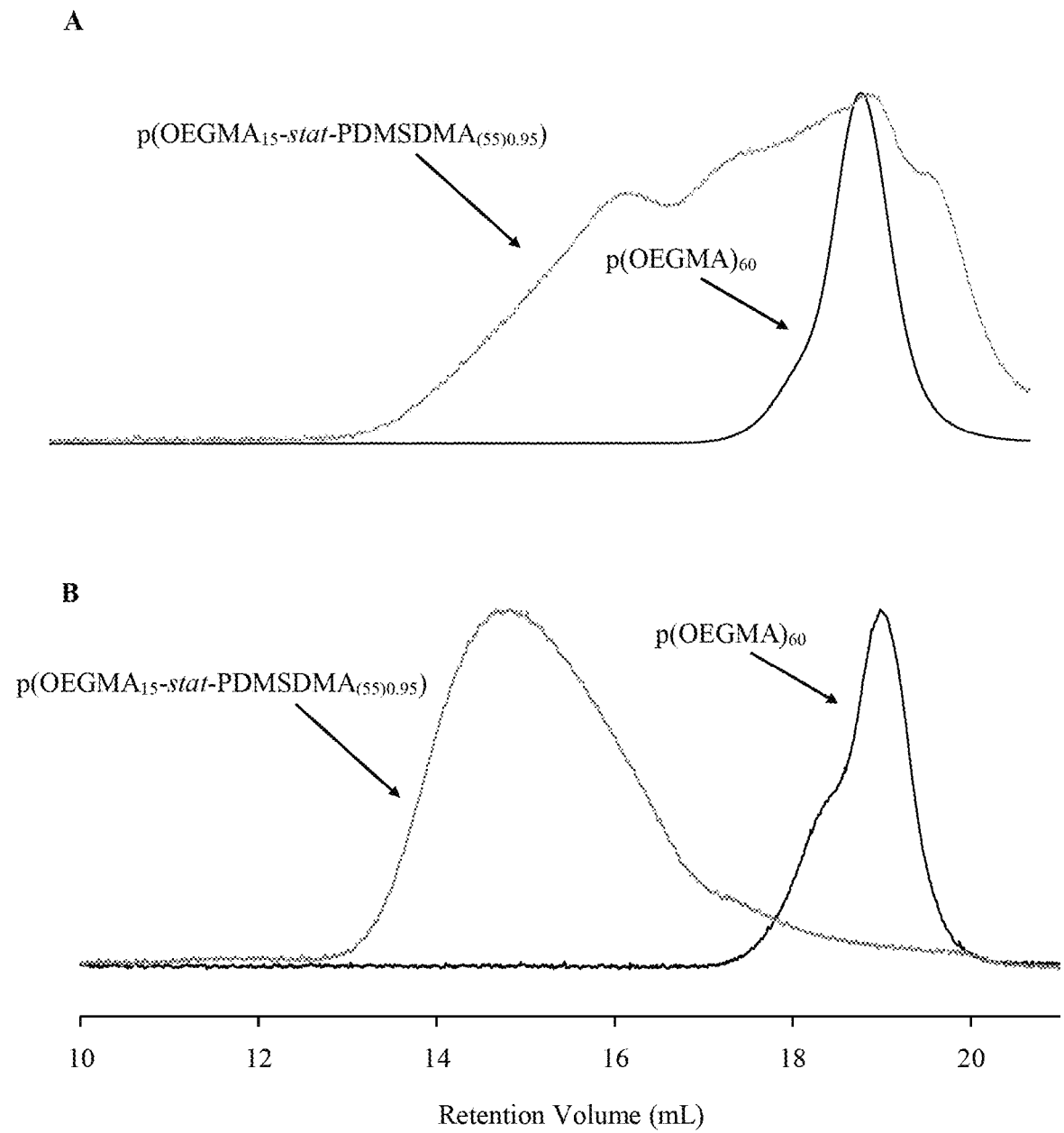
Figure 3:
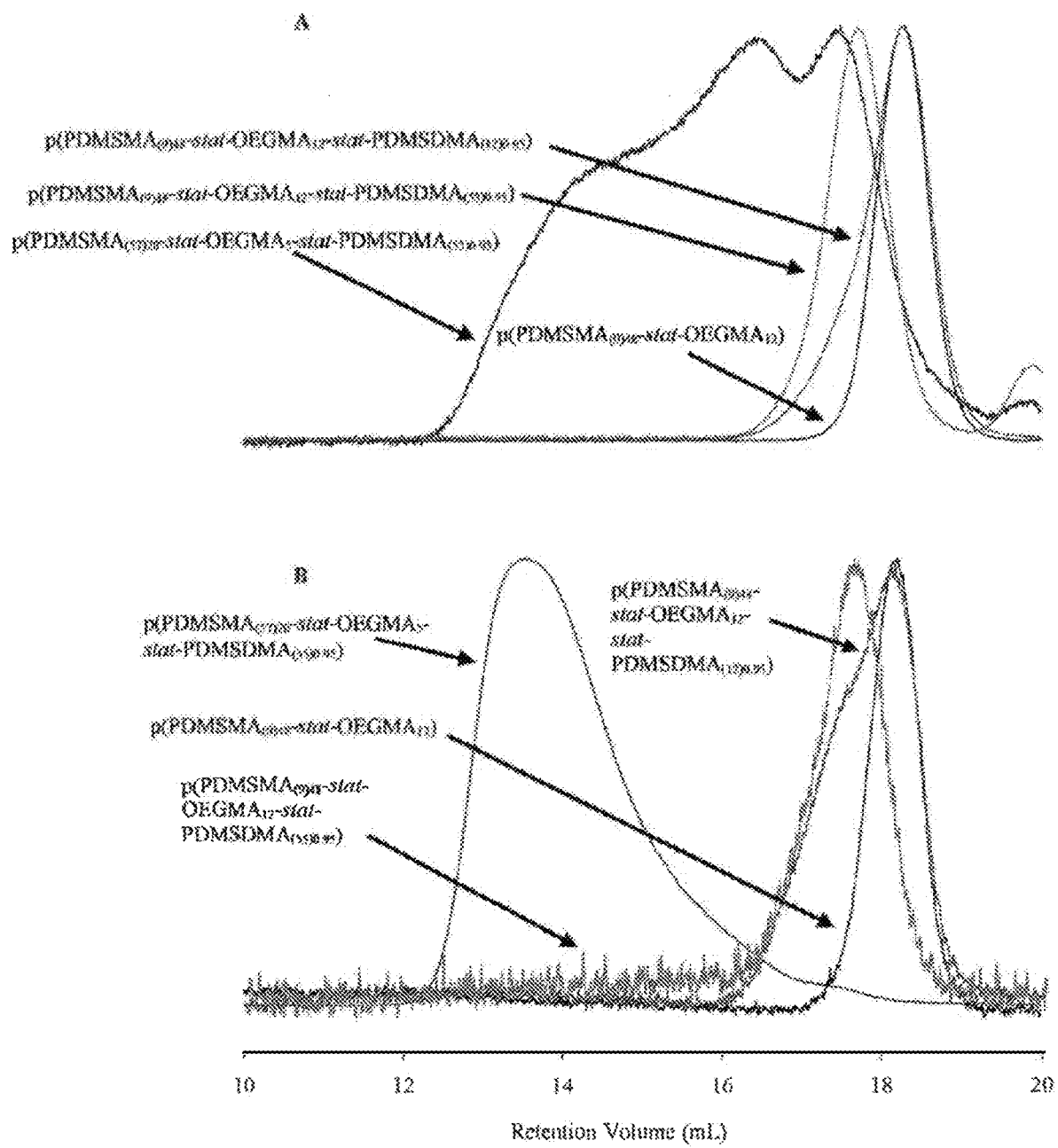
Figure 3:
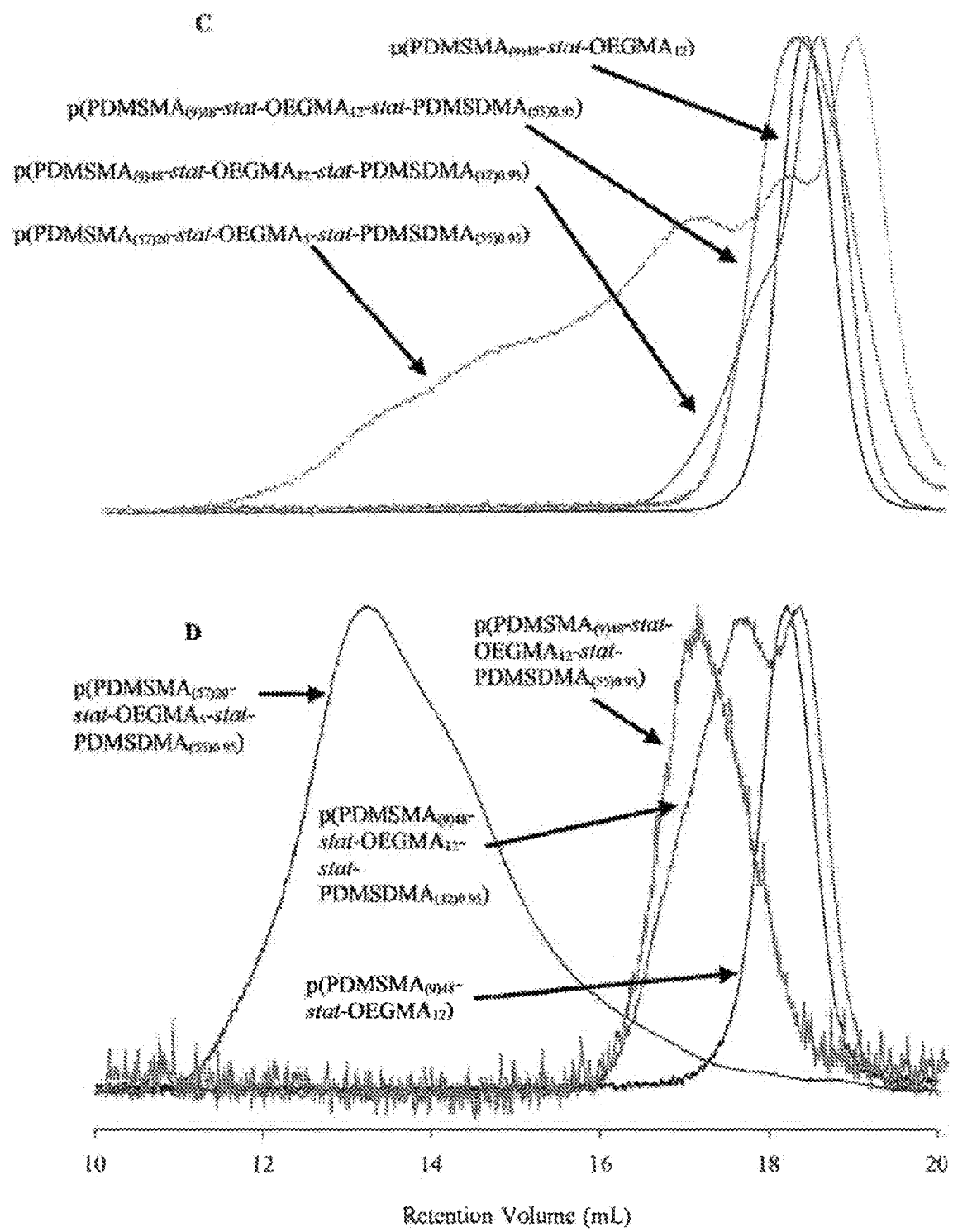
Figure 4:
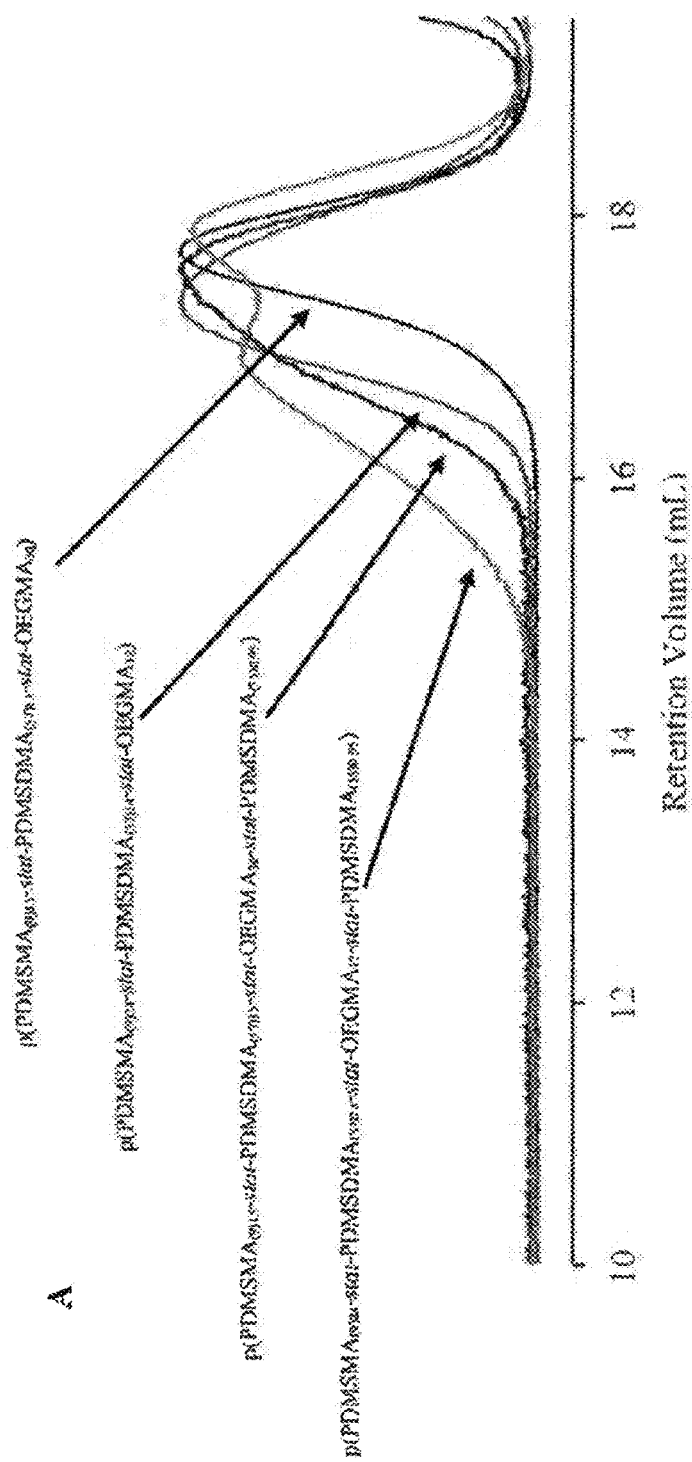
Figure 4:
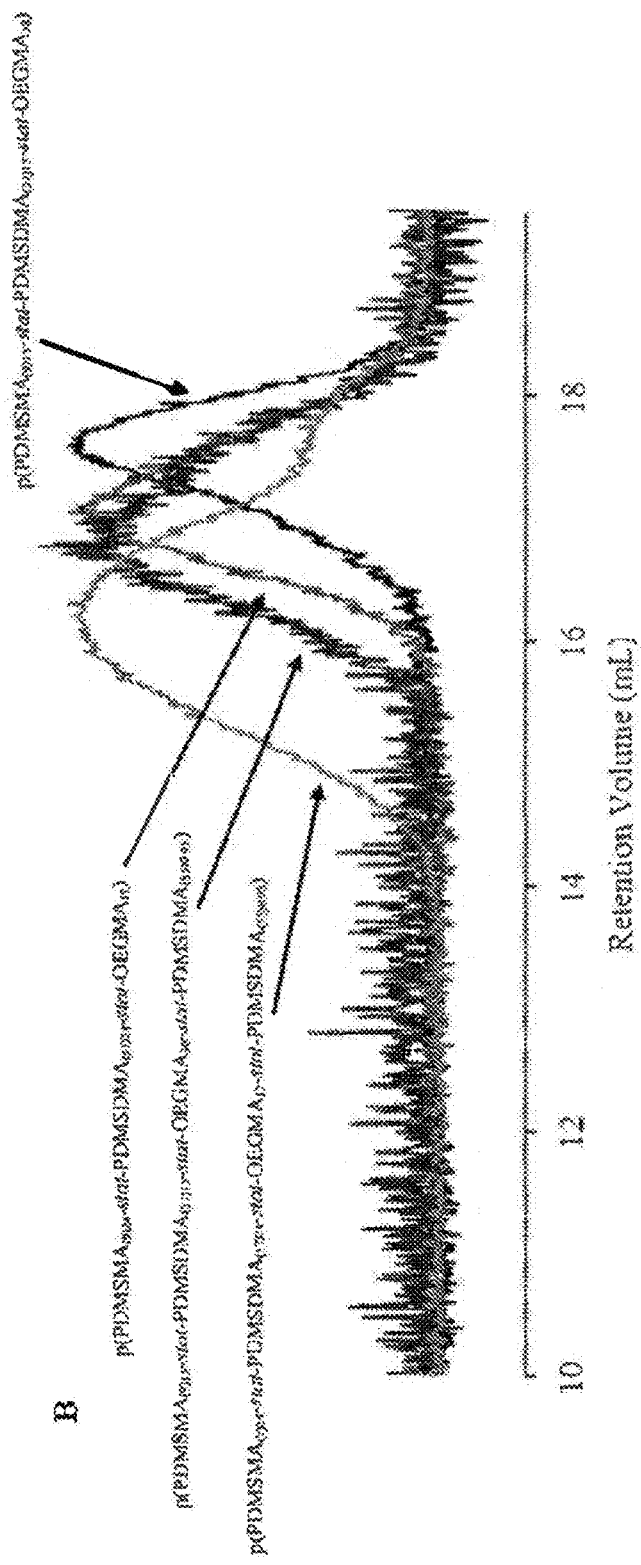
Figure 5:
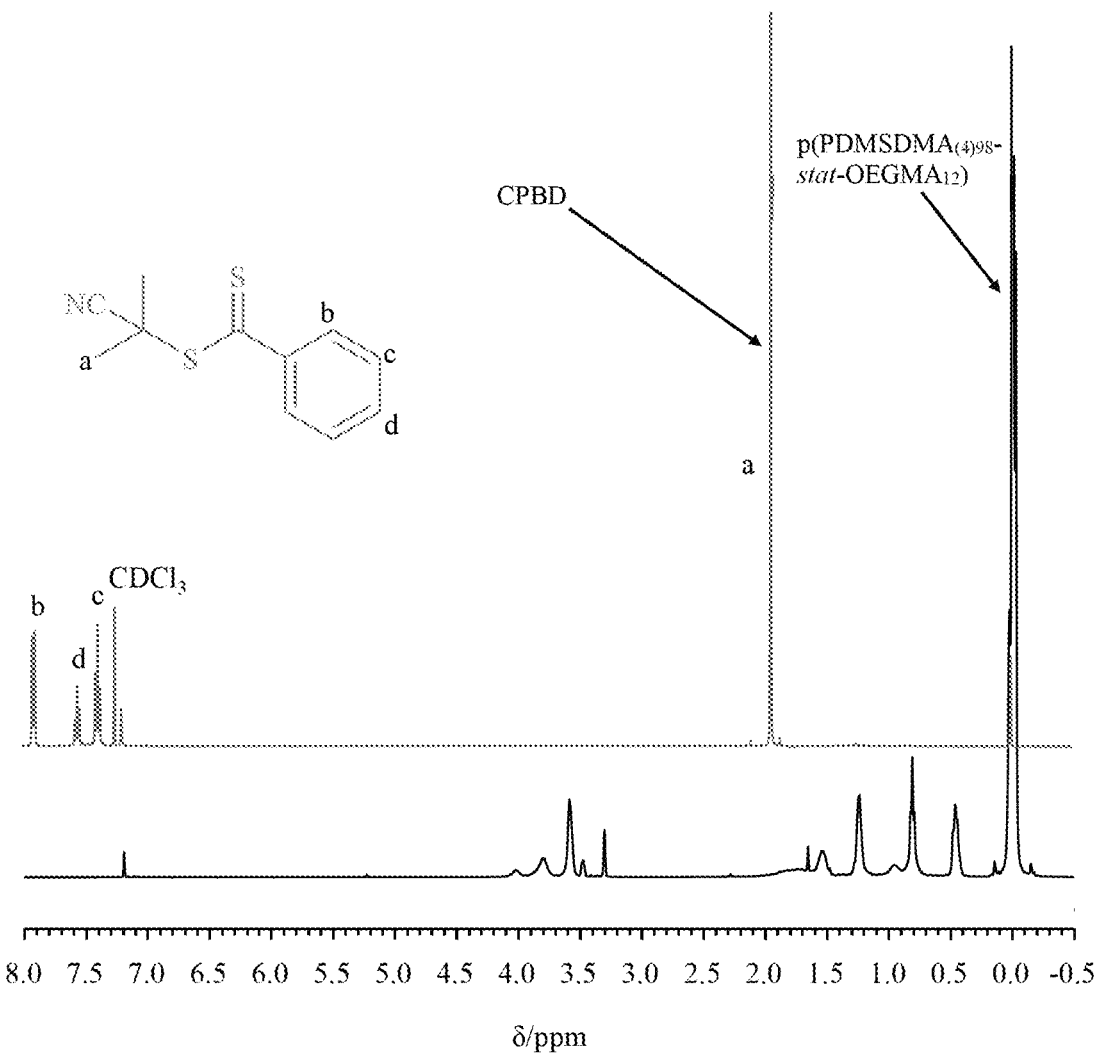
Figure 6:
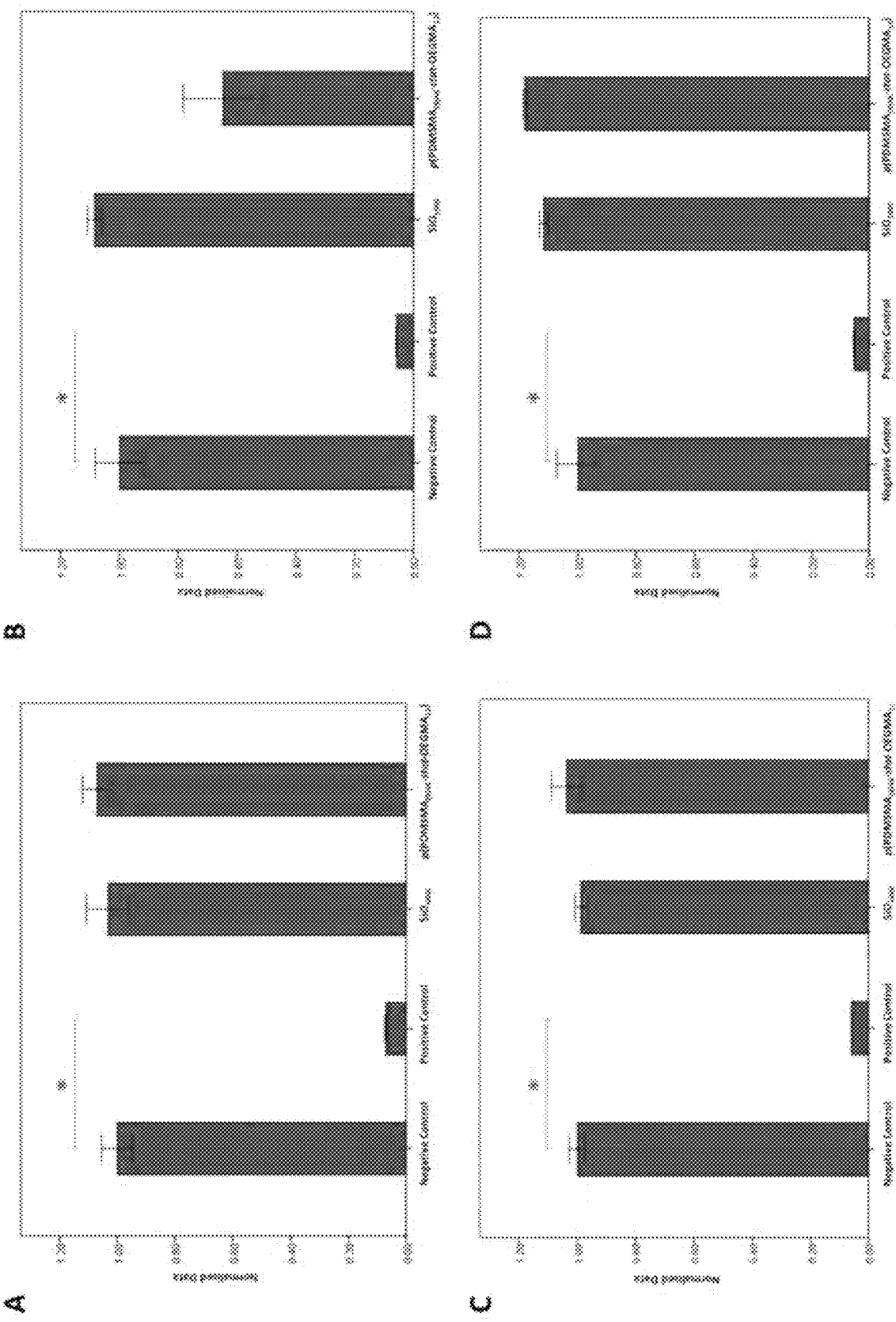

The present invention will now be described by way of example with reference to the following examples and figures:

FIG. 1 is GPC RI chromatogram overlay of A) $p(OEGMA_{60})$ and B) $p(PDMSMA_{(9)60})$ synthesised by ATRP (broad peak) and the RAFT synthesised equivalents (narrow peak);

FIG. 2 GPC chromatogram overlays of A) RI chromatograms and B) RALS chromatograms for linear $p(OEGMA_{60})$ (narrow peak) and branched $p(OEGMA_{15}\text{-co-PDMSDMA}_{(55)0.95})$ (broad peak);

FIG. 3 GPC chromatogram overlays of A) RI and B) RALS signals for linear $p(PDMSMA_{(9)47}\text{-co-OEGMA}_{12})$ (black) and branched equivalents with either $PDMSDMA_{(12)0.95}$ (red) or $PDMSDMA_{(55)0.95}$ (blue) and $p(PDMSMA_{(57)20}\text{-co-OEGMA}_{5}\text{-co-PDMSDMA}_{(55)9.95})$ (green). GPC analysis C) RI and D) RALS for linear $p(PDMSMA_{(9)30}\text{-co-OEGMA}_{30})$ (black) and branched equivalents with either $PDMSDMA_{(12)0.95}$ (red) or $PDMSDMA_{(55)0.95}$ (blue) and $p(PDMSMA_{(57)20}\text{-co-OEGMA}_{20}\text{-co-PDMSDMA}_{(55)0.95})$ (green);

FIG. 4 GPC chromatogram overlays of A) RI and B) RALS signals for linear $p(PDMSMA_{(9)15}\text{-co-PDMSMA}_{(57)15}\text{-co-OEGMA}_{30})$ (black) and $p(PDMSMA_{(9)24}\text{-co-PDMSMA}_{(57)24}\text{-co-OEGMA}_{12})$ (red) with their branched equivalents with $PDMSDMA_{(55)0.95}$ (blue and green respectively);

FIG. 5 $^1H$ NMR spectra ($CDCl_3$, 400 MHz) of CPBD (top spectra) and $p(PDMSMA_{(9)48}\text{-co-OEGMA}_{12})$ after CTA removal (bottom spectra);

FIG. 6 Resazurin assay with appropriate controls used to infer cytotoxicity of silicone oil (technical grade $SiO_{1000}$ having a viscosity of from 900-1200 cSt at 25° C., and blends of $p(PDMSMA_{(9)48}\text{-stat-OEGMA}_{12})$ with silicone oil (technical grade $SiO_{1000}$) at 10% (v/v). Pre- and post-confluent ARPE-19 cells (grown for 1 and 7 days respectively) were exposed to the oils for 1 and 7 d. A: Pre-confluent cells exposed for 1 day, B: Pre-confluent cells exposed for 7 days, C: Post-confluent cells exposed for 1 day and D: Post-confluent cells exposed for 7 days (mean, error bars represent ±1 standard deviation); n=3. *, Significance by ANOVA and Dunnett's T3 post-hoc evaluation (p≤0.05); and FIG. 7 ARPE-19 cells stained with phalloidin (green, F-actin cytoskeleton) and DAPI (blue, nuclei). Pre-confluent cells: Negative control (A), Exposed to silicone oil (technical grade $SiO_{1000}$) (B), Exposed to a 10% (v/v) blend of $p(PDMSMA_{(9)48}\text{-stat-OEGMA}_{12})$ for 1 day (C) and post-confluent cells: Negative control (D), Exposed to silicone oil (technical grade $SiO_{1000}$) (E), Exposed to a 10% (v/v) blend of $p(PDMSMA_{(9)48}\text{-stat-OEGMA}_{12})$ for 7 days (F) Scale bars represent 50 μm.

EXAMPLES

List of Abbreviations

5-FU 5-Fluorouracil
ACN Acetonitrile
AIBN 2,2'-Azobis(2-Methylpropionitrile)
Ar Argon
atRA All-trans Retinoic Acid
ATRP Atom Transfer Radical Polymerisation
bFGF Basic Fibroblast Growth Factor
Bpy Bipyridyl
$CDCl_3$ Deuterated Chloroform
CPBD 2-Cyano-2-Propyl Benzodithioate CTA Chain Transfer Agent
D₂O Deuterium Oxide
DAPI Dianidine-2-Phenylindole
DCM Dicholoromethane
DMF Dimethylformamide
DMSO Dimethyl Sulfoxide
EtBrB Ethyl α-bromoisobutyrate
EPGF Epidermal Growth Factor
FGF Fibroblast Growth Factor
FSiO Fluorinated Silicone Oil
HCl Hydrochloric Acid
Ibu Ibuprofen
IF-γ Interferon-Gamma
IL-Interleukin
IPA Isopropanol
MeOH Methanol
Me-PEO Methyl Terminated Poly(ethyleneoxide)
OEGMA Oligoethylene Glycol Methacrylate
PDMS Poly(dimethylsiloxane)
PDMSDMA Methacryloxypropyl Terminated Poly(dimethylsiloxane)
PDMSMA Mono-Methacryloxypropyl Terminated Poly(dimethylsiloxane)
PEO Poly(ethyleneoxide)
PDGF Platelet-Derived Growth Factor
PGA Polyglycolic Acid
PLA Polylactic Acid
PLGA Polylactic-stat-glycolic Acid
PVA Polyvinyl Acetate
RA Retinoic Acid
RAFT Reversible Addition-Fragmentation Chain Transfer
SFA Semi-Fluorinated Alkane
SiO Silicone Oil
TAA Triamcinolone Acetonide
ᵗBuOH Tertiary Butanol
TGF-ß Tumour Growth Factor-Beta
THF Tetrahydrofuran
VEGF Vascular Endothelial Growth Factor Preparation RAFT Polymerisation of OEGMA and PDMSMA Due to the insolubility of the catalytic system within the ATRP solvent, an alternative polymerisation method was employed; the non-catalytic controlled radical polymerisation technique RAFT. Matching the exact conditions of an ATRP with RAFT polymerisation is not possible, as this method of polymerisation requires a chain transfer agent (CTA). 2-cyano-2-propyl benzodithioate (CPBD) was selected as the RAFT CTA due to the excellent compatibility with methacrylate monomers. 2,2'-azobis(2-methylpropionitrile) (AIBN) was also selected as the free radical initiator due to excellent solubility within ᵗBuOH and copolymerisations were conducted at 30 wt. % monomer with respect to solvent and at 70° C., Scheme 1.

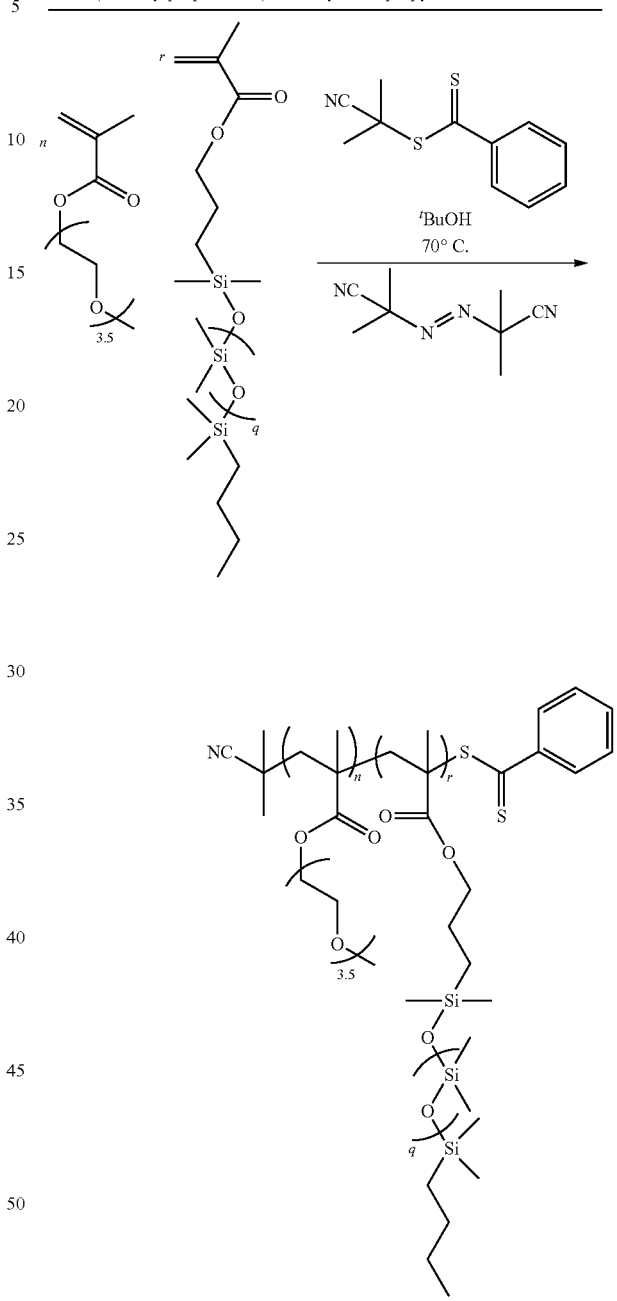

Scheme 1 Controlled radical polymerisation of OEGMA and PDMSMA conducted in ᵗBuOH at 70° C. via RAFT with 4,4'-azobis(4-methylpropionitrile) and 2-cyano-2-propyl benzodithioate.

Linear Amphiphilic Copolymers of OEGMA and PDMSMA Via RAFT

Homopolymerisations of OEGMA and the two different chain length PDMSMA monomers, targeting $DP_n$=60 monomer units, and copolymers of PDMSMA and OEGMA with identical targeted degrees of polymerisation at 80/20 and 50/50 ratios were synthesised. The resulting materials were analysed by $^1$H NMR spectroscopy and GPC (THF eluent at 35° C.), Table 1.

TABLE 1

$^1$H NMR and GPC data of all polymers synthesised via RAFT in $^t$BuOH

| Target Polymer Composition | Brancher | GPC (THF)$^a$ | | | $^1$H NMR | | |
|---|---|---|---|---|---|---|---|
| | | $M_n$ (g/mol) | $M_w$ (g/mol) | Đ | Polymer Composition | Conversion (%) PDMS | OEGMA |
| p(OEGMA$_{60}$) | — | 24,800 | 30,400 | 1.23 | p(OEGMA$_{55}$) | — | 92 |
| p(PDMSMA$_{(9)60}$) | — | 51,200 | 59,400 | 1.16 | p(PDMSMA$_{(9)58}$) | 96 | — |
| p(PDMSMA$_{(57)60}$) | — | 376,000 | 439,900 | 1.17 | p(PDMSMA$_{(57)23}$) | 38 | — |
| p(PDMSMA$_{(9)48}$-stat-OEGMA$_{12}$) | — | 47,650 | 52,700 | 1.11 | p(PDMSMA$_{(9)47}$-stat-OEGMA$_{11}$) | 9894 | 9498 |
| p(PDMSMA$_{(9)30}$-stat-OEGMA$_{30}$) | — | 33,300 | 36,800 | 1.11 | p(PDMSMA$_{(9)24}$-stat-OEGMA$_{29}$) | 80 | 96 |
| p(PDMSMA$_{(57)48}$-stat-OEGMA$_{12}$) | — | 350,600 | 380,200 | 1.08 | p(PDMSMA$_{(57)22}$-stat-OEGMA$_{9}$) | 45 | 77 |
| p(PDMSMA$_{(57)30}$-stat-OEGMA$_{30}$) | — | 220,250 | 266,850 | 1.21 | p(PDMSMA$_{(57)14}$-stat-OEGMA$_{20}$) | 47 | 65 |
| p(PDMSMA$_{(9)48}$-stat-OEGMA$_{12}$) | PDMS-DMA$_{(12)0.95}$ | 56,200 | 74,200 | 1.32 | — | 94 | 98 |
| p(PDMSMA$_{(9)30}$-stat-OEGMA$_{30}$) | PDMS-DMA$_{(12)0.95}$ | 50,700 | 75,600 | 1.49 | — | 91 | 97 |
| p(PDMSMA$_{(9)48}$-stat-OEGMA$_{12}$) | PDMS-DMA$_{(55)0.95}$ | 423,900 | 3,590,000 | 8.47 | — | 91 | 98 |
| p(PDMSMA$_{(9)30}$-stat-OEGMA$_{30}$) | PDMS-DMA$_{(55)0.95}$ | 142,100 | 5,220,000 | 36.73 | — | 90 | 97 |

$^a$Determined by GPC (THF eluent at 35° C.)
$^b$Determined by $^1$H NMR in CDCl$_3$ All materials synthesised have low dispersities (<1.25) indicating control within the polymerisation, and the difference between ATRP and RAFT was readily obvious when comparing the RI traces of p(OEGMA) and p(PDMSMA) ($M_n$ 985 gmol$^{-1}$, r=9) homopolymers, prepared by each technique (FIG. 1). High conversions could not be reached with the longer chain PDMSMA monomers (45-47% after 7 days), probably due to steric hindrance as RAFT requires a close proximity of two separate propagating polymer chain ends to undergo CTA exchange; however, these materials were still suitable for study after purification.

Branched Amphiphilic Terpolymers of OEGMA, PDMSMA and PDMSDMA Via RAFT

Due to the successful synthesis of the linear homopolymers and copolymers via RAFT, the introduction of the divinyl PDMS branchers ($M_n$=1,275 and 4,460 gmol$^{-1}$; m=12 and 55 respectively) to form branched terpolymers was undertaken. The brancher to CTA ratio was kept at 0.95:1 for each attempt to ensure gelation did not occur.

p(OEGMA$_{15}$) was successfully branched with PDMSDMA$_{(55)}$, which was not possible when previously attempted by ATRP. The formation of a branched architecture is clearly evidenced by the GPC (THF eluent at 35° C.) analysis of the copolymer (see FIG. 2). This successful copolymerisation led to the synthesis of branched p(PDMSMA-stat-OEGMA-stat-PDMSDMA) terpolymer architectures with varying compositions, Table 2.

TABLE 2

$^1$H NMR and GPC data of all branched polymers synthesised via RAFT

| Target Polymer Composition | Brancher | GPC (THF)$^a$ | | | $^1$H NMR | | |
|---|---|---|---|---|---|---|---|
| | | $M_n$ (g/mol) | $M_w$ (g/mol) | Đ | Polymer Composition | Conversion (%) PDMS | OEGMA |
| p(OEGMA$_{15}$) | PDMSDMA$_{(55)}$ | 44,000 | 470,300 | 10.69 | — | — | 81 |
| p(PDMSMA$_{(9)48}$-stat-OEGMA$_{12}$) | PDMSDMA$_{(12)}$ | 56,200 | 74,200 | 1.32 | — | 94 | 98 |
| p(PDMSMA$_{(9)30}$-stat-OEGMA$_{30}$) | PDMSDMA$_{(12)}$ | 50,700 | 75,600 | 1.49 | — | 91 | 97 |
| p(PDMSMA$_{(9)48}$-stat-OEGMA$_{12}$) | PDMSDMA$_{(55)}$ | 423,900 | 3,590,000 | 8.47 | — | 91 | 98 |
| p(PDMSMA$_{(9)30}$-stat-OEGMA$_{30}$) | PDMSDMA$_{(55)}$ | 142,100 | 5,220,000 | 36.73 | — | 90 | 97 |
| p(PDMSMA$_{(57)20}$-stat-OEGMA$_{5}$) | PDMSDMA$_{(55)}$ | 95,400 | 108,600 | 1.14 | — | 71 | 91 |
| p(PDMSMA$_{(57)20}$-stat-OEGMA$_{20}$) | PDMSDMA$_{(55)}$ | 149,700 | 199,300 | 1.33 | — | 82 | 97 |
| p(PDMSMA$_{(9)15}$-stat-PDMSMA$_{(57)15}$-stat-OEGMA$_{30}$) | — | 95,400 | 108,600 | 1.14 | p(PDMSMA$_{(9.57)23}$-stat-OEGMA$_{29}$) | 77 | 95 |

TABLE 2-continued

1H NMR and GPC data of all branched polymers synthesised via RAFT

| Target Polymer Composition | Brancher | GPC (THF)[a] | | | Polymer Composition | 1H NMR | |
|---|---|---|---|---|---|---|---|
| | | $M_n$ (g/mol) | $M_w$ (g/mol) | Đ | | Conversion (%) | |
| | | | | | | PDMS | OEGMA |
| p(PDMSMA$_{(9)24}$-stat-PDMSMA$_{(57)24}$-stat-OEGMA$_{12}$) | — | 149,700 | 199,300 | 1.33 | p(PDMSMA$_{(9.57)37}$-stat-OEGMA$_{11}$) | 78 | 92 |
| p(PDMSMA$_{(9)15}$-stat-PDMSMA$_{(57)15}$-stat-OEGMA$_{30}$) | PDMSDMA$_{(55)}$ | 235,600 | 323,200 | 1.37 | — | 79 | 91 |
| p(PDMSMA$_{(9)24}$-stat-PDMSMA$_{(57)24}$-stat-OEGMA$_{12}$) | PDMSDMA$_{(55)}$ | 174,100 | 389,900 | 2.24 | — | 92 | 89 |

[a]Determined by GPC (THF eluent at 35° C.)
[b]Determined by 1H NMR in CDCl$_3$

When branched terpolymer architectures were targeted using PDMSDMA$_{(12)}$ (only PDMSMA$_{(9)}$ was used in this case due to obvious steric constraints), low dispersities were achieved, and no high molecular weight materials were obtained, suggesting that the branching had been unsuccessful. The use of the PDMS monofunctional monomer and bifunctional brancher of similar sizes (r=9 and m=12) may be expected to lead to steric constraints that prevent branching. When using the longer brancher, PDMSDMA$_{(55)}$, high molecular weight branched materials were obtained when the smaller monomer (PDMSMA$_{(9)}$) was used, which appears to confirm this assumption. Similar problems were evident when branched architectures of p(PDMSMA$_{(57)}$-co-OEGMA) were targeted, even with the longer PDMSDMA$_{(55)}$ branchers. Again, having PDMS monomer and brancher of similar sizes (r=57 and m=55) appears to lead to steric hindrance.

The GPC chromatograms of the different architectures synthesised using RAFT are presented in FIG. 3. It can clearly be seen that only the combination of a small PDMS monomer (r=9) and a long PDMS brancher (m=55) leads to successful branching. The only architectures which display branching consist of p(PDMSMA$_{(9)48}$-co-OEGMA$_{12}$-co-PDMSDMA$_{(55)0.95}$) and p(PDMSMA$_{(9)30}$-co-OEGMA$_{30}$-co-PDMSDMA$_{(55)0.95}$) as evidenced by the very high molecular weights and Đ values obtained.

In an attempt to obtain branched polymers using the long chain (PDMSMA$_{(57)}$) monomer, the longer (PDMSDMA$_{(55)}$) brancher was used Unfortunately, after leaving this reaction for 30 days, a high enough conversion was not reached in order to obtain highly branched materials (see FIG. 4).

Solubility of Amphiphilic Copolymers and Terpolymers in SiO

As the aim of these studies was to investigate the ability to solubilise a hydrophilic polymer within SiO and evaluate drug release from the resulting mixture, it was essential to investigate the solubility of the amphiphilic co- and terpolymers, both linear and branched, in SiO. Table 3 summarises the materials tested for solubility in SiO and the results obtained.

TABLE 3

Solubility of the synthesised polymers in SiO (% v/v)

| Target Polymer Composition | Brancher | Target composition (mol % of total monomer) | | Miscibility in Silicone |
|---|---|---|---|---|
| | | EG | DMS | Oil (% v/v) |
| p(OEGMA$_{60}$) | — | 100 | 0 | <1 |
| p(PDMSMA$_{(9)60}$) | — | 0 | 100 | Miscible |
| p(PDMSMA$_{(57)60}$) | — | 0 | 100 | Miscible |
| p(PDMSMA$_{(9)48}$-stat-OEGMA$_{12}$) | — | 10 | 90 | <30 |
| p(PDMSMA$_{(9)30}$-stat-OEGMA$_{30}$) | — | 30.8 | 69.2 | <5 |
| p(PDMSMA$_{(57)48}$-stat-OEGMA$_{12}$) | — | 1.7 | 98.3 | Miscible |
| p(PDMSMA$_{(57)30}$-stat-OEGMA$_{30}$) | — | 6.5 | 93.5 | Miscible |
| p(PDMSMA$_{(9)48}$-stat-OEGMA$_{12}$) | PDMSDMA$_{(55)}$ | 9 | 91 | <40 |
| p(PDMSMA$_{(9)30}$-stat-OEGMA$_{30}$) | PDMSDMA$_{(55)}$ | 27 | 73 | <40 |
| p(PDMSMA$_{(9)24}$-stat-PDMSMA$_{(57)24}$-stat-OEGMA$_{12}$) | — | 2.9 | 97.1 | Miscible |
| p(PDMSMA$_{(9)15}$-stat-PDMSMA$_{(57)15}$-stat-OEGMA$_{30}$) | — | 10.8 | 89.2 | Miscible |

The branched p(OEGMA$_{15}$-co-PDMSDMA$_{(55)0.95}$) had minimal SiO solubility (<1% v/v) and, as this contained the largest hydrophobic component possible through branching alone, co- and terpolymers of OEGMA with PDMSMA were clearly needed to increase solubility.

All other polymers were soluble at 40-50% (v/v) apart from when a 50/50 ratio of OEGMA:PDMSMA$_{(9)}$ was copolymerised which represents the smallest content of hydrophobic monomer. This success represents a major increase in solubility compared to less than 1% (v/v) that had been seen without the incorporation of PDMSMA.

Removal of CTA from Amphiphilic Co- and Terpolymers Synthesised Via RAFT

As the amphiphilic copolymers were soluble in SiO at high levels, the removal of the RAFT chain end was required as the CTA-end group is known to be highly coloured and the solutions were a bright pink colour (Scheme 2). In some cases, gelation was also observed when the amphiphilic copolymers and linear homopolymers of PDMSMA were stored, suggesting the presence of difunctionalised monomer impurities within the commercial PDMSMA. The removal and recovery of CPBD following RAFT polymerisations of PMMA has been reported. Excess AIBN was added to a solution of the purified polymer and subsequent AIBN thermal decomposition yields cyanoisopropyl radicals which react with the C═S bond of the thiocarbonyl-thio group. This results in an intermediate radical which can either fragment back to the previous state or free the thiocarbonyl-thio moiety from the polymer chain-end. The excess cyano-isopropyl radicals drive the equilibrium towards a radical chain end which is capped by additional cyano-isopropyl groups. It has been reported that too little AIBN under these conditions can lead to disproportionation and subsequent reactions between polymer chains. The temperature and length of the reaction are important for the complete removal of the thiocarbonyl-thio end group and should follow the half-life time of the radical initiator used (in this case AIBN).

Similar conditions to those previously reported were employed for the removal of CPBD from p(PDMSMA$_{(9)48}$-co-OEGMA$_{12}$). The purified polymer was dissolved in toluene and a 20 molar excess of AIBN added to the solution which was degassed and heated to 80° C. for 150 minutes (the half-life time of AIBN in these conditions is 80 minutes). The polymer was isolated by precipitation into cold MeOH which afforded a white solution (Scheme 2).

Scheme 2 Scheme of CPBD removal and pictures of p(PDMSMA$_{(9)48}$-stat-OEGMA$_{12}$) synthesised via RAFT polymerisation A: before and B: after reaction with AIBN

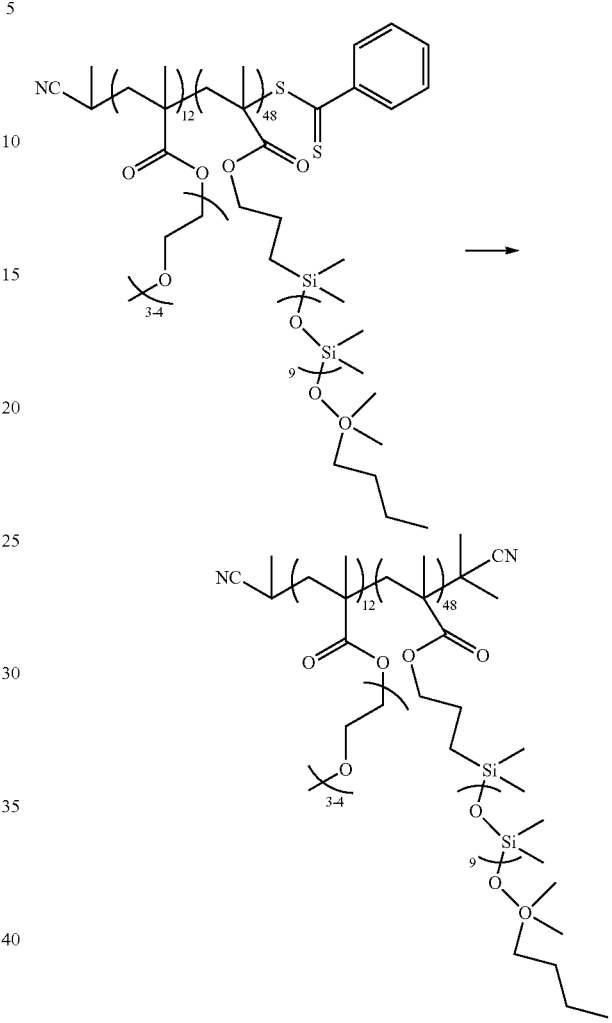

The colour change indicated removal of the CPBD and the recovered polymer was analysed by $^1$H NMR spectroscopy (FIG. 5) which confirmed the CTA removal as the peaks at 7.30, 7.38, and 7.93 ppm, characteristic of the dithiobenzoate moiety, were no longer present.

RAFT

All RAFT polymerisations were conducted at a constant ratio of chain transfer agent to initiator [CPBD]:[AIBN]=1:0.2.

Linear Polymerisation: p(OEGMA)

In a typical synthesis, targeting DP$_n$=60 monomer units, AIBN (2.7 mg, 0.016 mmol), CPBD (18.4 mg, 0.083 mmol) and OEGMA (1.5 g, 5 mmol) were added to a 25 mL Schlenk tube equipped with a magnetic stirrer bar. $^t$BuOH (4.5 mL, 30 wt % wrt. monomer, deoxygenated via N$_2$ purge) was added and the resulting solution degassed by five cycles of freeze/pump/thaw. After the final thaw cycle, the flask was backfilled with N$_2$. The reaction flask was placed into a pre-heated oil bath (70° C.) and stirred for 8 hours, after which the reaction medium was observed to be slightly turbid. The polymerization was stopped by cooling the flask to ambient temperature, exposing its contents to air and diluting the reaction medium with 'BuOH. The solution was concentrated by rotary evaporation and precipitated into cold petroleum-ether (40-60) to give a pink solid. The sample was dried under vacuum at 40° C. for 24 hours and analysed by $^1$H NMR in $D_2O$ and GPC with a mobile phase of DMF.

Linear Polymerisation p(OEGMA-stat-PDMSMA)

In a typical synthesis, targeting $DP_n$=60 monomer units (OEGMA/PDMSMA 50/50), AIBN (2.7 mg, 0.016 mmol), CPBD (18.4 mg, 0.083 mmol), OEGMA (0.148 g, 0.492 mmol) and PDMSMA ($M_n$ 985 gmol$^{-1}$, 1.5 g, 1.524 mmol) were added to a 25 mL Schlenk tube equipped with a magnetic stirrer bar. 'BuOH (4.96 mL, 30 wt % wrt. monomer, deoxygenated via $N_2$ purge) was added and the resulting solution degassed by five cycles of freeze/pump/thaw. After the final thaw cycle, the flask was backfilled with $N_2$. The reaction flask was placed into a pre-heated oil bath (70° C.) and stirred for 24 hours, after which the reaction medium was observed to be slightly turbid. The polymerisation was stopped by cooling the flask to ambient temperature, exposing its contents to air and diluting the reaction medium with 'BuOH. The solution was concentrated by rotary evaporation and precipitated into cold MeOH to give a pink liquid. The sample was dried under vacuum at 40° C. for 24 hours and analysed by $^1$H NMR in $CDCl_3$ and GPC with a mobile phase of THF.

Branched Polymerisation: p(OEGMA-stat-PDMSMA-stat-PDMSDMA)

In a typical synthesis, targeting $DP_n$=60 monomer units (OEGMA/PDMSMA 50/50), AIBN (5.6 mg, 0.034 mmol), CPBD (37.5 mg, 0.169 mmol), OEGMA (1.524 g, 5 mmol), PDMSMA ($M_n$ 985 gmol$^{-1}$, 5 g, 5 mmol) and PDMSDMA ($M_n$ 1,275 gmol$^{-1}$, 0.205 g, 0.158 mmol) were added to a 100 mL Schlenk tube equipped with a magnetic stirrer bar. 'BuOH (20.3 mL, 30 wt % wrt. monomer, deoxygenated via $N_2$ purge) was added and the resulting solution degassed by five cycles of freeze/pump/thaw. After the final thaw cycle, the flask was backfilled with $N_2$. The reaction flask was placed into a pre-heated oil bath (70° C.) and stirred for 24 hours, after which the reaction medium was observed to be slightly turbid. The polymerization was stopped by cooling the flask to ambient temperature, exposing its contents to air and diluting the reaction medium with 'BuOH. The solution was concentrated by rotary evaporation and precipitated into MeOH) to give a pink liquid. The sample was dried under vacuum at 40° C. for 24 hours and analysed by $^1$H NMR spectroscopy in $CDCl_3$ and GPC with a mobile phase of THF.

CTA Removal from $p(PDMS_{(9)48}\text{-stat-}OEGMA_{12})$

A ratio of polymer:AIBN=1:20 was used. $p(PDMS_{(9)48}\text{-co-}OEGMA_{12})$ (5.3811 g, 0.112 mmol) was dissolved in toluene (73 mL, deoxygenated via Ar purge) in a 100 mL schlenk flask equipped with a stirrer bar. AIBN (369 mg, 2.24 mmol) was added to the reaction flask and purged with Ar. The temperature was raised to 80° C. for 2.5 hours. After the reaction with AIBN, the polymer was precipitated in cold MeOH and a white liquid was isolated by decanting the MeOH. The product was dried in vacuo then analysed by $^1$H NMR spectroscopy in $CDCl_3$.

Process

All-trans retinoic acid (atRA) was purchased from Xian Bosheng Biological Technology Co., Ltd. and used as received. Ibuprofen (Ibu) was purchased from Tokyo Chemical Industry UK Ltd. and used as received. Silicone oil (technical grade: 1000; Viscosity=900-1200 cSt at 25° C.; 5000; Viscosity=4800-5500 cSt at 25° C.) was donated by Fluron GmbH and used as received. All deuterated solvents were purchased from Sigma-Aldrich and used as received apart from $CDCl_3$ where 0.1% TMS was added. All solvents used were analytical grade and purchased from Fisher. Resazurin was purchased from Sigma and used as received. Alexa Fluor® 488 Phalloidin (Phalloidin) and 4',6-diamidino-2-phenylindole dihydrochloride (DAPI) was purchased from Invitrogen and used as received; phalloidin was dissolved in methanol before use, according to the manufacturer's instructions. ARPE-19 cells were bought from American Type Culture Collection, Manassas, Va., USA, catalogue number CRL 2302 and frozen stocks were stored in-house. Dulbecco's Modified Eagle Medium/Ham's Nutrient Mixture F-12 Formulation (DMEM/F12, catalogue number D8437), Penicillin Streptomycin 10 mg/mL streptomycin in 0.9% NaCl (Pen-Strep), Amphotericin B solution 250 µg/mL in deionized water, Dulbecco's calcium and magnesium free phosphate buffered saline (PBS), Trypsin-EDTA containing 5 g porcine trypsin and 2 g ethylenediaminetetraacetic acid (Trypsin) and neutral buffered formalin (NBF) were purchased from Sigma-Aldrich and used as received. Foetal bovine serum (FCS) was purchased from BioSera and used as received. All tissue culture plates were purchased from Greiner, except black 96 well plates which were purchased from Costar. Poly (ethylene glycol) methyl ether methacrylate ($M_n$=300 gmol$^{-1}$) (98%) (OEGMA), 2-cyano-2-propyl benzodithioate (97%) (CPBD) and 2,2'-azobis(2-methylpropionitrile) (98%) (AIBN) were purchased from Sigma-Aldrich and used as received. Mono methacryloxypropyl polydimethylsiloxane methacrylate (molecular weight 985 and 4,600 gmol$^{-1}$ PDMSMA$_9$ and PDMSMA$_{57}$ respectively) and methacryloxypropyl polydimethylsiloxane dimethacrylate (molecular weight 1,275 and 4,460 gmol$^{-1}$; PDMSDMA$_{12}$ and PDMSDMA$_{55}$ respectively) were purchased from Gelest and used as received.

Characterization

NMR spectra were recorded using a Bruker DPX-400 spectrometer operating at 400 MHz for $^1$H NMR and 100 MHz for $^{13}$C NMR in $CDCl_3$. UV-Vis spectra were collected using a Thermo Fisher NanonDrop 2000c spectrophotometer, either with a quartz cuvette or directly with the nanodrop functionality of the equipment depending on the solvent used. Data was analyzed using the NanoDrop2000 software. ProSafe+ scintillation cocktail (Meridian Biotechnologies Ltd.) was used as received. All radiation measurements were carried out using a liquid scintillation counter (Packard Tri-carb 3100TR; Isotech). Triple detection GPC was performed to measure molecular weights and molecular weight distributions using Malvern Viscotek instruments. One instrument was equipped with a GPCmax VE2001 auto-sampler, two Viscotek D6000 columns (and a guard column) and a triple detector array TDA305 (refractive index, light scattering and viscometer) with a mobile phase of DMF containing 0.01 M lithium bromide at 60° C. and a flow-rate of 1 mL min$^{-1}$. The second instrument was equipped with a GPCmax VE2001 autosampler, two Viscotek T6000 columns (and a guard column), a refractive index (RI) detector VE3580 and a 270 Dual Detector (light scattering and viscometer) with a mobile phase of THF containing 2 v/v % of trimethylamine at 35° C. with a flow rate of 1 mL min$^{-1}$. A Nikon Eclipse Ti-E inverted microscope system was used to collect cell images.

Synthesis of Polymers

All RAFT polymerizations were conducted at a constant ratio of chain transfer agent to initiator of [CPBD]:[AIBN] =1:0.2.

For the synthesis of p(OEGMA), targeting $DP_n$=60 monomer units, AIBN (2.7 mg, 0.016 mmol), CPBD (18.4 mg, 0.083 mmol) and OEGMA (1.5 g, 5 mmol) were added to a 25 mL Schlenk tube equipped with a magnetic stirrer bar. $^t$BuOH (4.5 mL, 30 wt % wrt. monomer, deoxygenated via $N_2$ purge) was added and the resulting solution degassed by five cycles of freeze/pump/thaw. After the final thaw cycle, the flask was backfilled with $N_2$. The reaction flask was placed into a pre-heated oil bath (70° C.) and stirred for 8 hours, after which the reaction medium was observed to be slightly turbid. The polymerization was stopped by cooling the flask to ambient temperature, exposing its contents to air and diluting the reaction medium with $^t$BuOH. The solution was concentrated by rotary evaporation and precipitated into cold petroleum-ether (40-60) to give a pink liquid. The sample was dried under vacuum at 40° C. for 24 hours and analysed by $^1$H NMR in $D_2O$ and GPC with a mobile phase of DMF.

In a typical synthesis of p(OEGMA-stat-PDMSMA$_9$), targeting $DP_n$=60 monomer units (OEGMA/PDMSMA$_9$ 50/50), AIBN (2.7 mg, 0.016 mmol), CPBD (18.4 mg, 0.083 mmol), OEGMA (0.148 g, 0.492 mmol) and PDMSMA$_9$ ($M_n$=985 gmol$^{-1}$, 1.5 g, 1.524 mmol) were added to a 25 mL Schlenk tube equipped with a magnetic stirrer bar. $^t$BuOH (4.96 mL, 30 wt % wrt. monomer, deoxygenated via $N_2$ purge) was added and the resulting solution degassed by five cycles of freeze/pump/thaw. After the final thaw cycle, the flask was backfilled with $N_2$. The reaction flask was placed into a pre-heated oil bath (70° C.) and stirred for 24 hours, after which the reaction medium was observed to be slightly turbid. The polymerization was stopped by cooling the flask to ambient temperature, exposing its contents to air and diluting the reaction medium with $^t$BuOH. The solution was concentrated by rotary evaporation and precipitated into cold MeOH to give a pink liquid. The sample was dried under vacuum at 40° C. for 24 hours and analyzed by $^1$H NMR in CDCl$_3$ and GPC with a mobile phase of THF.

In a typical branched polymerization synthesis of p(OEGMA-stat-PDMSMA$_9$-stat-PDMSDMA$_{12}$), targeting $DP_n$=60 monomer units (OEGMA/PDMSMA$_9$ 50/50), AIBN (5.6 mg, 0.034 mmol), CPBD (37.5 mg, 0.169 mmol), OEGMA (1.524 g, 5 mmol), PDMSMA$_9$ ($M_n$=985 gmol$^{-1}$, 5 g, 5 mmol) and PDMSDMA$_{12}$ ($M_n$=1,275 gmol$^{-1}$, 0.205 g, 0.158 mmol) were added to a 100 mL Schlenk tube equipped with a magnetic stirrer bar. $^t$BuOH (20.3 mL, 30 wt % wrt. monomer, deoxygenated via $N_2$ purge) was added and the resulting solution degassed by five cycles of freeze/pump/thaw. After the final thaw cycle, the flask was backfilled with $N_2$. The reaction flask was placed into a pre-heated oil bath (70° C.) and stirred for 24 hours, after which the reaction medium was observed to be slightly turbid. The polymerization was stopped by cooling the flask to ambient temperature, exposing its contents to air and diluting the reaction medium with $^t$BuOH. The solution was concentrated by rotary evaporation and precipitated into MeOH) to give a pink liquid. The sample was dried under vacuum at 40° C. for 24 hours and analyzed by $^1$H NMR spectroscopy in CDCl$_3$ and GPC with a mobile phase of THF.

CTA removal involved a ratio of polymer:AIBN=1:20. In a typical CTA removal p(PDMS$_{(9)48}$-stat-OEGMA$_{12}$) (5.3811 g, 0.112 mmol) was dissolved in toluene (73 mL, deoxygenated via Ar purge) in a 100 mL schlenk flask equipped with a stirrer bar. AIBN (369 mg, 2.24 mmol) was added to the reaction flask and purged with Ar. The temperature was raised to 80° C. for 2.5 hours. After the reaction with AIBN, the polymer was precipitated in cold MeOH and a white liquid was isolated by decanting the MeOH. The product was dried in vacuo then analyzed by $^1$H NMR spectroscopy in CDCl$_3$.

In a typical solubilization experiment, polymer (1 mL) and SiO$_{1000}$ (1 mL) were syringed into a glass vial to create a 50 v/v % mixture and placed on a roller for 3 days. The solutions were diluted systematically by adding SiO$_{1000}$ to decrease the amount of polymer by 10 v/v %, rolled for 3 days each time, until a soluble concentration was reached (i.e. 40, 30, 20, 10 also 5 and 1 v/v % were tested).

Radiometric Studies and Analysis of Drug Solubility in Silicone Oils

To determine solubility of drugs in silicone oil saturated solutions of atRA and Ibu in silicone oil were prepared by mixing atRA (11.6 mg) or Ibu (32 mg) with tritiated versions of the drug (10 μCi) in EtOH (2 mL); after evaporation of the solvent at ambient temperature, SiO$_{1000}$ (5 mL) was added to the residual solid and the solution was stirred for 2 weeks. The sample was filtered using a syringe pump (4 mL/h) and 0.45 μm PTFE filters. Samples of the filtered oils (20 μL) were then solubilized in diethyl ether (8 mL) before scintillation cocktail (10 mL) was added. Radiation was then measured on a scintillation counter and saturation concentrations were determined.

Amounts of drug added to the samples were altered depending on targeted final concentrations. Solutions of 200 μg/mL: atRA (1 mg) and tritiated atRA (6 μCi) were mixed in EtOH (2 mL) and the same protocol was followed. Solutions of 20 μg/mL: atRA (0.1 mg) and tritiated atRA (2 μCi) were mixed in EtOH (2 mL) and the same procedure was carried out. Solutions of 1 mg/mL: Ibu (5 mg) and tritiated Ibu (7.5 μCi) were mixed in EtOH (2 mL) and the same protocol was followed.

For the preparation of both atRA and Ibu solutions in p(PDMSMA$_{(9)48}$-stat-OEGMA$_{12}$) blends, 5 and 10% vol content of polymer blends were prepared by mixing for 3 days and loaded with drug by following the same protocols as described above.

Cytotoxicity Assays of Drug Compounds and Polymers

Cells were cultured at 37° C. in a dark, humid 5% CO$_2$ incubator; media containing 1% Pen-Strep, 1% Amphotericin B and supplemented with 10% FCS was used. For these studies, cells were used between passages 22 and 25. Multiple assays were carried out on ARPE-19 cells to study cytotoxicity and the effects of different drug concentrations and blends of p(PDMSMA$_{(9)48}$-stat-OEGMA$_{12}$) in SiO (silicon oil). 18,000 cells/well were seeded in a 48 well tissue culture plate and left for 1 or 7 days to adhere to the plate. The 7 day samples were fed once within the week by replacing 450 μL old medium with 500 μL fresh culture medium. After the predetermined time period, the media was aspirated from all wells and replaced with 0.6 mL media containing drug, fresh media with p(PDMSMA$_{(9)48}$-stat-OEGMA$_{12}$) blends (0.2 mL) over the top or conditions required for controls. Controls included: media, SiO (0.2 mL) and a negative control (20% DMSO). Cells were then incubated for 1 to 7 days before the following assays could be performed.

Sterile resazurin solution was added to wells at a concentration of 10 μg/mL Plates were incubated in the dark at 37° C. for 4 hours. Media was removed and put in black 96-well plastic plates; resorufin fluorescence was read using a Fluostar Optima spectrofluorometer ($\lambda_{Excitation}$=530 nm; $\lambda_{Emission}$=590 nm). All values were normalised to negative control wells on each plate.

Following removal of resazurin solution, cells were washed with PBS (500 μL) then fixed for 10 minutes in 10% neutral buffered formalin (NBF; 10% formalin, approximately 4% formaldehyde). NBF was discarded and cells stained with phalloidin (6.667 μg/mL) for 30 minutes at 4° C. Cells were washed with PBS then counterstained with DAPI (0.01 μg/mL) for 10 minutes. Cells were imaged using a Zeiss Axiovert 400 microscope.

Statistical analyses were carried out on SPSS Statistics V22 software; one way test of homogeneity of variances and ANOVA as well as Dunnett's T3 post-hoc evaluation were conducted, p<0.05 was regarded to be statistically significant.

Radiometric Studies of Drug Release 1 mL of silicone oil or p(PDMSMA$_{(9)48}$-stat-OEGMA$_{12}$) blend (5 or 10%) with determined concentration of drug was placed in a 24 well plate over 0.5 mL media. Samples of media (0.5 mL) were taken and replaced at determined time intervals; daily for the first critical week then every 2-3 days for the remainder of the study, using a 1 mL syringe and 25 gauge needle for up to 71 days. Sampling and withdrawing of the media was done very carefully in order to avoid any emulsification of the oil. Media (250 μL) was mixed with scintillation cocktail (10 mL) and analyzed by liquid scintillation counting.

Cytotoxicity of p(PDMSMA(9)48-stat-OEGMA12) with ARPE-19 Cells

The metabolic activity and morphology of ARPE-19 cells was studied for pre- and post-confluent cells (1 day and 7 day growth respectively) which were exposed to silicone oil (SiO$_{1000}$) and blends of p(PDMSMA$_{(9)48}$-stat-OEGMA$_{12}$) with silicone oil (SiO$_{1000}$) at 10% (v/v) for 1 and 7 days. A resazurin assay was carried out, followed by phalloidin staining of the cells from the assay.

Figure 7:
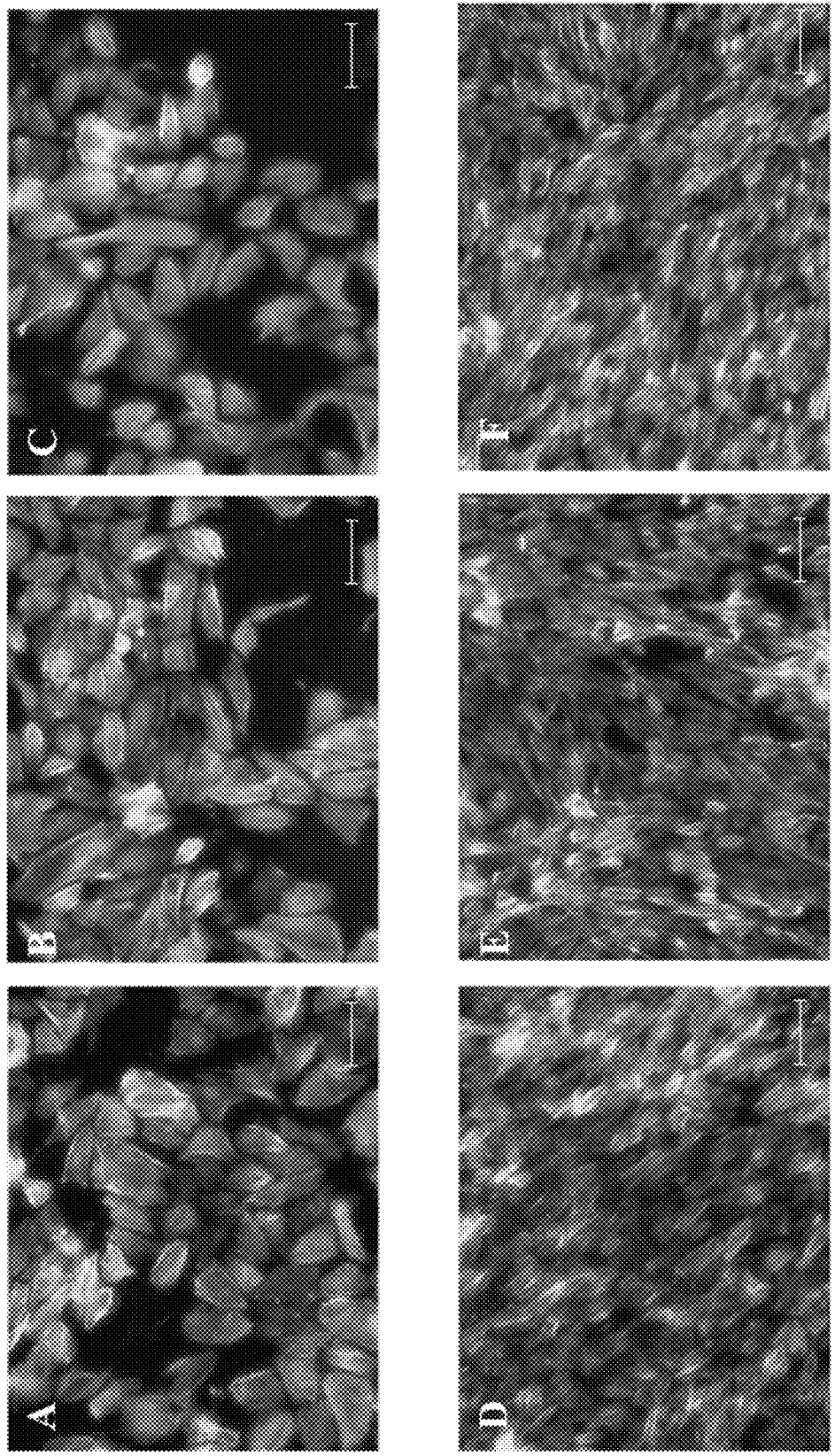

The resazurin assay contained negative (healthy cells) and positive controls (cells exposed to 20% DMSO) as well as media with no resazurin present to determine background signals. As seen in FIG. 7, these controls confirmed the validity of the assay and statistical analyses were carried out on SPSS Statistics V22 software; one way test of homogeneity of variances and ANOVA as well as Dunnett's T3 post-hoc evaluation were conducted, p<0.05 was regarded to be statistically significant. There was a significant difference between the negative control and the positive control, however, no significant difference was observed between the positive control and cells exposed to silicone oil (SiO$_{1000}$), p(PDMSMA(9)48-stat-OEGMA12) blends at 10% v/v in silicone oil (SiO$_{1000}$), indicating that the oil and blends have no cytotoxic effect on the ARPE-19 cells.

Phalloidin staining confirmed no cytotoxic effects, as evidenced by the presence of healthy cytoskeletons when cells were exposed to the oil and blend. Images of phalloidin stained cells exposed to silicone oil (SiO$_{1000}$) and the 10% blends, are presented in FIG. 8, alongside negative control (healthy cells) for the two extreme time points examined. All images represent healthy cytoskeletons.

The invention claimed is:

1. A liquid ophthalmic composition comprising:
   i) a base oil comprising a silicone oil;
   ii) an additive comprising a copolymer comprising hydrophobic and hydrophilic units; and
   iii) a drug;
   wherein the liquid composition is adapted for use in or as an ophthalmic tamponade.

2. The composition of claim 1, wherein the base oil further comprises one or more of a further silicone oil, a fluorinated silicone oil, a perfluorocarbon oil, or mixtures thereof.

3. The composition of claim 1, wherein the base oil has a kinematic viscosity of from about 100 to about 10,000 cSt, or from about 1,000 to about 5,000 cSt, or from about 1,000 to about 2,000 cSt.

4. The composition of claim 1, wherein the copolymer is linear or branched.

5. The composition as claimed in claim 1, wherein the copolymer is a vinyl polymer.

6. The composition as claimed in claim 1, wherein the copolymer has a comb structure in which the hydrophobic and hydrophilic units are pendant chains on a backbone of the copolymer.

7. The composition of claim 1, wherein the hydrophilic unit is a polyethylene glycol unit.

8. The composition of claim 1, wherein the copolymer comprises a hydrophilic monomer unit, and the hydrophilic monomer unit is oligoethyleneglycol monomethyl ether methacrylate, or other oligoethyleneglycol methacrylate monomer.

9. The composition of claim 1, wherein the hydrophobic unit is selected from a methacrylate monomer, dimethacrylate monomer, or mixtures thereof.

10. The composition of claim 1, wherein the copolymer comprises a hydrophobic monomer unit, and the hydrophobic monomer unit is a polydimethylsiloxane methacrylate monomer, or polydimethylsiloxane dimethacrylate monomer, or other polydimethylsiloxane acrylate monomer.

11. The composition of claim 1, wherein the copolymer independently comprises from about 4 to about 100 hydrophilic and/or hydrophobic monomeric units, or from about 5 to about 90 hydrophilic and/or hydrophobic monomeric units, or from about 10 to about 80 hydrophilic and/or hydrophobic monomeric units, or from about 15 to about 70 hydrophilic and/or hydrophobic monomeric units, or from about 20 to about 60 hydrophilic and/or hydrophobic monomeric units.

12. The composition of claim 1, wherein the molar ratio of the monomeric units (hydrophobic:hydrophilic) is from about 80:20 to about 50:50; or from about 75:25 to about 50:50; or from about 70:30 to about 50:50; or from about 65:35 to about 50:50; or from about 60:40 to about 50:50; or from about 55:45 to about 50:50.

13. The composition of claim 1, wherein the copolymer has a weight average molecular weight of from about 30,000 to about 5,300,000 g/mol, or from about 35,000 to about 350,000 g/mol, or from about 40,000 to about 250,000 g/mol.

14. The composition of claim 1, wherein additive is present in an amount of from about 0.05% to about 20% v/v relative to the base oil, or from about 1% to about 15% v/v, or from about 2% to about 12% v/v, or from about 3% to about 10% v/v, or from about 4% to about 8% v/v, or from about 4% to about 7% v/v.

15. The composition of claim 1, wherein the copolymer comprises residues of a polydimethylsiloxane methacrylate monomer of the following formula:

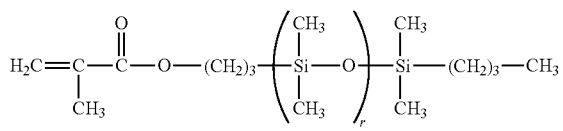

wherein r is selected from about 1 to about 100, or from about 2 to about 90, or from about 4 to about 85, or from about 6 to about 80, or from about 8 to about 75, or from about 8 to about 70, or from about 9 to about 65, or from about 10 to about 60, or from about 12 to about 57, or from about 14 to about 55.

16. The composition of claim 1, wherein the copolymer comprises residues of a polydimethylsiloxane dimethacrylate monomer of the following formula:

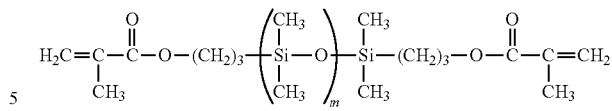

wherein m is selected from about 1 to about 300, or from about 5 to about 290, or from about 10 to about 280, or from about 20 to about 250, or from about 20 to about 200, or from about 30 to about 180, or from about 40 to about 150, or from about 50 to about 100.

17. The composition of claim 1, wherein the drug is selected from an anti-inflammatory drug, an anti-proliferative, an anti-oxidant drug, an anti-neoplastic drug, an anti-growth factor, or mixtures thereof.

18. The composition of claim 1, wherein the drug is selected from all-trans retinoic acid and non-steroidal anti-inflammatories.

19. The composition of claim 1, wherein the drug is present in an amount of from about 1 to about 1000 µg per ml; or from about 5 to about 900 µg per ml; or from about 10 to about 800 µg per ml; or from about 15 to about 700 µg per ml.

20. The composition according to claim 1, wherein the copolymer is formed by controlled radical polymerisation, conventional free radical polymerisation, or other addition polymerisation.

21. The composition of claim 1, wherein the copolymer is a statistical copolymer.

* * * * *